(12) United States Patent
Landau et al.

(10) Patent No.: US 7,094,786 B2
(45) Date of Patent: *Aug. 22, 2006

(54) METHOD OF TREATING NAUSEA, VOMITING, RETCHING OR ANY COMBINATION THEREOF

(75) Inventors: Steven B. Landau, Wellesley, MA (US); Cheryl L. Miller, Natick, MA (US); Karl B. Thor, Morrisville, NC (US)

(73) Assignee: Dynogen Pharmaceuticals, Inc., Waltham, MA (US)

(*) Notice: Subject to any disclaimer, the term of this patent is extended or adjusted under 35 U.S.C. 154(b) by 89 days.

This patent is subject to a terminal disclaimer.

(21) Appl. No.: 10/846,979

(22) Filed: May 14, 2004

(65) Prior Publication Data

US 2004/0254172 A1 Dec. 16, 2004

Related U.S. Application Data

(63) Continuation of application No. 10/757,981, filed on Jan. 13, 2004.

(60) Provisional application No. 60/492,478, filed on Aug. 4, 2003, provisional application No. 60/440,076, filed on Jan. 13, 2003.

(51) Int. Cl.
A61K 31/496 (2006.01)

(52) U.S. Cl. .................................. 514/252.16

(58) Field of Classification Search ............ 514/252.16
See application file for complete search history.

(56) References Cited

U.S. PATENT DOCUMENTS

| | | | |
|---|---|---|---|
| 4,695,568 A | 9/1987 | Ninomiya et al. | 514/258 |
| 4,753,789 A | 6/1988 | Tyers et al. | 424/10 |
| 4,783,478 A | 11/1988 | Wootton et al. | 514/397 |
| 4,845,092 A | 7/1989 | Sanger et al. | 514/216 |
| 4,939,136 A | 7/1990 | Haeck et al. | 514/183 |
| 5,225,407 A | 7/1993 | Oakley et al. | 514/215 |
| 5,352,685 A | 10/1994 | Maruyama et al. | 514/301 |
| 5,470,868 A | 11/1995 | Young | 514/307 |
| 5,530,008 A | 6/1996 | Azcona et al. | 514/304 |
| 5,576,317 A | 11/1996 | Gonsalves | 514/231.2 |
| 5,663,343 A | 9/1997 | van der Meij et al. | 546/72 |
| 5,945,415 A | 8/1999 | Kato et al. | 514/218 |
| 5,962,494 A | 10/1999 | Young | 514/397 |
| 5,977,127 A | 11/1999 | Bonnacker et al. | 514/284 |
| 5,985,866 A | 11/1999 | Müller et al. | 514/214 |
| 5,990,159 A | 11/1999 | Meulemans et al. | 514/469 |
| 6,054,461 A | 4/2000 | Fairbanks et al. | 514/269 |
| 6,117,879 A | 9/2000 | Fairbanks et al. | 514/269 |
| 6,156,771 A | 12/2000 | Rubin et al. | 514/330 |
| 6,284,770 B1 | 9/2001 | Mangel et al. | 514/292 |
| 6,355,647 B1 | 3/2002 | Steiner et al. | 514/267 |
| 6,376,550 B1 | 4/2002 | Raber et al. | 514/646 |
| 6,429,209 B1 | 8/2002 | Mangel et al. | 514/292 |
| 6,440,453 B1 | 8/2002 | Fischer et al. | 424/449 |
| 6,441,038 B1 | 8/2002 | Loder et al. | 514/561 |
| 6,465,458 B1 | 10/2002 | Wong et al. | 514/239.2 |
| 6,552,045 B1 | 4/2003 | Rubin et al. | 514/327 |
| 6,593,336 B1 | 7/2003 | Mangel et al. | 514/292 |
| 2001/0020025 A1 | 9/2001 | Megens | 514/272 |
| 2001/0044450 A1 | 11/2001 | Mangel et al. | 514/292 |
| 2002/0002197 A1 | 1/2002 | Mueller et al. | 514/397 |
| 2002/0086880 A1 | 7/2002 | Rubin et al. | 514/327 |
| 2002/0086881 A1 | 7/2002 | Rubin et al. | 514/329 |
| 2002/0107244 A1 | 8/2002 | Howard, Jr. | 514/227.5 |
| 2003/0036500 A1 | 2/2003 | Rubin et al. | 514/1 |
| 2003/0036549 A1 | 2/2003 | Mangel et al. | 514/291 |
| 2003/0158221 A1 | 8/2003 | Zhang et al. | 514/291 |
| 2003/0203055 A1 | 10/2003 | Rao et al. | 424/738 |
| 2004/0048874 A1 | 3/2004 | Bardsley et al. | 514/252.16 |
| 2004/0254171 A1 | 12/2004 | Landau et al. | 514/218 |

FOREIGN PATENT DOCUMENTS

| | | |
|---|---|---|
| EP | 0 313 393 B1 | 3/1994 |
| GB | 0216027.3 | 7/2002 |
| GB | 0220064.0 | 8/2002 |
| GB | 0304648.9 | 2/2003 |
| GB | 0316115.5 | 7/2003 |
| JP | 06016557 A2 | 1/1994 |
| WO | WO 94/01095 A3 | 1/1994 |
| WO | WO 98/50037 | 11/1998 |
| WO | WO 99/02516 | 1/1999 |
| WO | WO 00/06160 A1 | 2/2000 |
| WO | WO 00/51583 A3 | 9/2000 |
| WO | WO 00/51584 A3 | 9/2000 |
| WO | WO 01/41748 A2 | 6/2001 |
| WO | WO 02/44170 A2 | 6/2002 |
| WO | WO 02/094249 A1 | 11/2002 |
| WO | WO 03/061657 A1 | 7/2003 |
| WO | WO 03/077897 A1 | 9/2003 |
| WO | WO 2004/004734 A1 | 1/2004 |
| WO | WO 2004/019948 A1 | 3/2004 |
| WO | WO 2004/058353 A3 | 7/2004 |

OTHER PUBLICATIONS

Angel, I., et al. "Litoxetine: A Selective 5-HT Uptake Inhibitor with Concomitant 5-HT$_3$ Receptor Antagonist and Antiemetic Properties," *Eur. J. Pharmacol.*, 232(2-3):139-145 (1993).

(Continued)

*Primary Examiner*—Phyllis G. Spivack
(74) *Attorney, Agent, or Firm*—Jones Day

(57) ABSTRACT

Methods are disclosed for the treatment of nausea and vomiting in a patient suffering therefrom comprising administering 4-(2-fluorophenyl)-6-methyl-2-(1-piperazinyl)thieno[2,3-D]pyrimidine.

3 Claims, 3 Drawing Sheets

OTHER PUBLICATIONS

Béïque, J.C., et al., "Affinities of Venlafaxine and Various Reuptake Inhibitors for the Serotonin and Norepinephrine Transporters," *Eur. J. Pharmacol.*, 349(1): 129-132 (1998).

Burns, M.J., "The Pharmacology and Toxicology of Reboxetine," *Int. J. Med. Toxicol.* 3(4):26 1-8 (2000).

Butler, A., et al, "Pharmacological Properties of GR38032F, a Novel Antagonist at 5-$HT_3$ Receptors," *Br. J. Pharmacol.*, 94(2): 397-412 (1988).

Bymaster, F.P., et al., "Comparative Affinity of Duloxetine and Venlafaxine for Serotonin and Norepinephrine Transporters *In Vitro* and *In Vivo*, Human Serotonin Receptor Subtypes, and Other Neuronal Receptors," *Neuropsychopharmacology*, 25(6):871-880 (2001).

Camilleri, M., "Serotonergic Modulation of Visceral Sensation: Lower Gut." *Gut* 51(1):81-86 (2002).

Center for Drug Evaluation and Research Application No.: 020623; Pharmacology Reviews; Jul. 5, 1996.

Crow, M.K., et al. "Management of Nausea and Vomiting," *Medical Oncology: A Comprehensive Review*, [Retrieved Jan. 29, 2003] Retrieved from the Internet <URL:http://www.cancernetwork.com/textbook/morev41.htm>.

Depoortere, I., et al., "Dose-Dependent Effects of Recombinant Human Interleukin-11 on Contractile Properties in Rabbit 2,4,6-Trinitrobenzene Sulfonic Acid Colitis[1], " *J. Pharmacol. Exp. Ther.*, 294(3): 983-990 (2000).

Eguchi, J., et al, "Pharmacological Profile of the Novel Antidepressant 4-(2-Fluorophenyl)-6-Methyl-2-(1-Piperazinyl)thieno-[2,3-d]pyrimidine Monodydrate Hydrocloride," *Arzneim-Forschung/Drug Res.*, 47(12): 1337-1347 (1997).

Eguchi, J., et al., "The Anxiolytic-Like Effect of MCI-225, A Selective NA Reuptake Inhibitor with 5-$HT_3$ Receptor Antagonism," *Pharm. Biochem. and Behavior*, 68:677-683 (2001).

Fairweather, D. B., et al., "The Psychomotor and Cognitive Effects of Litoxetine in Young and Middle Aged Volunteers," *Br. J. Clin. Pharmacol.*, 40(2):119-125 (1995).

Ito, C., et al., "Effect of GK-128 [2-[(2-Methylimidazol-1-yl]-benzo[f]thiochromen-1-one Monohydrochloride Hemihydrate], a Selective 5-Hydroxytryptamine$_3$ Receptor Antagonist, on Colonic Function in Rats," *J. Pharmacol. Exp. Ther.*, 280(1): 67-72 (1997).

Jin, J.G., et al., "Propulsion in Guinea Pig Colon Induced by 5-Hydroxytryptamine (HT) Via 5-$HT_4$ and 5-$HT_3$ Receptors [1]," *J. Pharmacol. Exp. Ther.*, 288(1): 93-97 (1999).

Kilpatrick, G., et al., "Identification and Distribution of 5-$HT_3$ Receptors in Rat Brain Using Radioligand Binding," *Nature*, 330: 746-748 (1987).

Kuver, R., et al., "Nausea and Vomiting in Adolescents and Adults," *Nausea and Vomiting*, [Retrieved Jan. 29, 2003] Retrieved from the Internet <URL:http://www.uwgi.org/cme/cmeCourseCD/ch_01/ch01txt.htm>.

Ladabaum, U. and Hasler, W.L., "Novel Approaches to the Nausea and Vomiting," *Dig. Dis.*, 17(3): 125-132 (1999).

LOTRONEX—Tablets, *Product Information*, GlaxoSmithKline, Research Triangle Park, NC, pp. 1-13 (2002).

Milano, S. et al., "The Piglet as a Suitable Animal Model for Studying the Delayed Phase of Cisplatin-Induced Emesis," *J. Pharmacol. Exp. Ther.*, 274(2): 951-961 (1995).

Million, M., et al., "Susceptibility of Lewis and Fischer Rats to Stress-induced Worsening of TNB-colitis: Protective Role of Brain CRF," *Amer. Phys. Soc.*, 276 (4 Pt 1): G1027-G1036 (1999).

Morrow, G.R., et al., "Progress in Reducing Nausea and Emesis," *Cancer* 76(3): 343-357 (1995).

Owens, M.J., et al., "Neurotransmitter Receptor and Transporter Binding Profile of Antidepressants and their Metabolites[1]," *J. Pharmacol. Exp. Ther.*, 283(3): 1305-1322 (1997).

Prakash, C., et al., "Tricyclic Antidepressants for Functional Nausea and Vomiting: Clinical Outcome in 37 Patients," *Dig. Dis. Sci.*, 43(9):1951-1956 (1998).

Prakash, C. and Clouse, R.E., "Cyclic Vomiting Syndrome in Adults: Clinical Features and Response to Tricyclic Antidepressants," *Am. J. Gastroenterol.*, 94(10):2855-2860 (1999).

Sallan, S.E., et al., "Antiemetics in Patients Receiving Chemotherapy for Cancer," *N. Eng. J. Med.*, 302(3): 135-138 (1980).

Spiller, R., "Pharmacotherapy: Non-serotonergic Mechanisms" *Gut*, 51 (Suppl 1): i87-90 (2002).

Venkova, K. et al., "Peripheral Activity of a New $NK_1$ Receptor Antagonist TAK-637 in the Gastrointestinal Tract," *J. Pharmacol. Exp. Ther.* , 300(3): 1046-1052 (2002).

Veyrat-Follet, C., et al., "Physiology of Chemotherapy-Induced Emesis and Antiemetic Therapy," *Drugs* 53(2): 206-234 (1997).

Wong, E.H.F., et al., "Reboxetine: A Pharmacologically Potent, Selective, and Specific Norepinephrine Reuptake Inhibitor," *Biol. Psychiatry.* 47(9): 818-829 (2000).

Wood, J.D., et al. "Fundamentals of Neurogastroenterology,"*Gut* 45(2):II6-II16 (1999).

METHOD OF TREATING NAUSEA, VOMITING, RETCHING OR ANY COMBINATION THEREOF

RELATED APPLICATION

This application is a continuation of, and claims benefit of, U.S. application Ser. No. 10/757,981, filed Jan. 13, 2004, which claims the benefit of U.S. Provisional Application No. 60/492,478 filed on Aug. 4, 2003 and U.S. Provisional Application No. 60/440,076 filed on Jan. 13, 2003, each of which is incorporated by reference in its entirety herein.

BACKGROUND OF THE INVENTION

Emesis is the act of vomiting and can be described as the forceful expulsion of gastrointestinal contents through the mouth brought about by the descent of the diaphragm and powerful contractions of the abdominal muscles. Emesis is usually, but not always, preceded by nausea (the unpleasant feeling that one is about to vomit). Retching or dry heaves involves the same physiological mechanisms as vomiting, but occurs against a closed glottis, which prohibits the expulsion of gastric contents. Vomiting, nausea, retching or combinations thereof can be caused by a number of factors including, but not limited to, anesthetics, radiation, cancer chemotherapeutic agents, toxic agents, odors, medicines, for example, serotonin reuptake inhibitors, analgesics such as morphine, antibiotics and antiparasitic agents, pregnancy and motion. Conditions which are associated with vertigo (e.g., Meniere's disease and vestibular neuronitis) can also cause nausea, vomiting, retching or any combination thereof. Headache, caused by, for example, migraine, increased intracranial pressure or cerebral vascular hemorrhage can also result in nausea, vomiting, retching or any combination thereof. In addition, certain maladies of the gastrointestinal (GI) tract, for example, cholecystitis, choledocholithiasis, intestinal obstruction, acute gastroenteritis, perforated viscus, dyspepsia resulting from, for example, gastroesophageal reflux disease, peptic ulcer disease, gastroparesis, gastric or esophageal neoplasms, infiltrative gastric disorders (e.g., Menetrier's syndrome, Crohn's disease, eosinophilic gastroenteritis, sarcoidosis and amyloidosis), gastric infections (e.g., CMV, fingal, TB and syphilis), parasites (e.g., *Giardia lamblia* and *Strongyloides stercoralis*), chronic gastric volvulus, chronic intestinal ischemia, altered gastric motility disorders and/or food intolerance or Zollinger-Ellison syndrome can result in vomiting, nausea, retching or any combination thereof. However, in some cases of vomiting, nausea, retching or any combination thereof, no etiology can be determined despite extensive diagnostic testing (e.g., Cyclic Vomiting Syndrome).

Nausea, vomiting and retching are defined as acute when symptoms are present for less than a week. The causes of nausea, vomiting and retching of short duration are often separable from etiologies leading to more chronic symptoms.

Nausea, vomiting and retching are defined as chronic when symptoms are present for over a week. For example, symptoms can be continuous or intermittent and last for months or years.

The vomiting reflex is triggered by stimulation of chemoreceptors in the upper GI tract and mechanoreceptors in the wall of the GI tract which are activated by both contraction and distension of the gut as well as by physical damage. A coordinating center in the central nervous system controls the emetic response. This center is located in the parvicellular reticular formation in the lateral medullary region of the brain. Afferent nerves to the vomiting center arise from abdominal splanchnic and vagal nerves, vestibulo-labyrinthine receptors, the cerebral cortex and the chemoreceptor trigger zone (CTZ). The CTZ lies adjacent in the area postrema and contains chemoreceptors that sample both blood and cerebrospinal fluid. Direct links exist between the emetic center and the CTZ. The CTZ is exposed to emetic stimuli of endogenous origin (e.g., hormones) as well as to stimuli of exogenous origin, such as drugs. The efferent branches of cranial nerves V, VII and IX, as well as the vagus nerve and sympathetic trunk produce the complex coordinated set of muscular contractions, cardiovascular responses and reverse peristalsis that characterize vomiting.

Of significant clinical relevance is the nausea and vomiting resulting from the administration of general anesthetics (commonly referred to as, post-operative nausea and vomiting, PONV), chemotherapeutic agents and radiation therapy.

In fact, the symptoms caused by the chemotherapeutic agents can be so severe that the patient refuses further treatment. Three types of emesis are associated with the use of chemotherapeutic agents. The first, is acute emesis, which occurs within the first 24 hours of chemotherapy. The second, is delayed emesis which occurs 24 hours or more after chemotherapy administration. The third, is anticipatory emesis, which begins prior to the administration of chemotherapy, usually in patients whose emesis was poorly controlled during a previous chemotherapy cycle.

PONV is also an important patient problem and one that patients rate as the most distressing aspect of operative procedure, even above pain. Consequently, the need for an effective anti-emetic in this area is important. As a clinical problem PONV is troublesome and requires staff around to ensure that vomitus is not regurgitated, which can have very serious clinical sequelae. Further, there are certain operative procedures where it is clinically important that patients do not vomit. For example, in ocular surgery where intracranial ocular pressure can increase to the extent that stitches are ruptured and the operative procedure is set back in terms of success to a marked degree.

There are a number groups of agents that are used clinically for the treatment of emesis. These groups include: anticholinergics, antihistamines, phenothiazines, butyrophenones, cannabinoids, benzamides, glucocorticoids, benzodiazepines and 5-$HT_3$ receptor antagonists. In addition, tricyclic antidepressants have also been used on a limited basis.

The phenothiazines, which include prochlorperazine and chlorpromazine, block dopamine type-2 receptors in the CTZ. However, the side effects, for example, extrapyramidal symptoms, such as, dystonia and akathisia, sedation, anticholinergic effect and orthostatic hypotension make the use of the phenothiazines a less than desirable therapy.

Anticholinergics used in the treatment of nausea and vomiting, include scopolomine (e.g., in treating motion sickness). However, drowsiness is a significant side effect.

Antihistamines (dimenhydrinate and diphenhydramine) are mainly used for motion sickness and in antiemetic combinations to reduce extrapyramidal side effects of dopamine receptor antagonists. As a single agent, the antihistamines have modest antiemetic activity and include sedation and anticholinergic effects as the major drawbacks.

Butyrophenones, for example, haloperidol and droperidol, work by blocking dopamine receptors in the CTZ. The side effects of butyrophenones include akathisia, dystonia and hypotension.

Cannabinoids such as tetrahydrocannabinol and nabilone have shown limited efficacy (see, e.g. Sallan et al., *N. Eng. J. Med.*, 302: 135–138 (1980)). In addition, the side effects include euphoria, dizziness, paranoid ideation and somnolence.

Benzamides include, for example, metoclopramide, cisapride and trimethobenzamide. However, side effects which include extrapyramidal symptoms and diarrhea make the use of benzamides a less than desirable therapy.

Benzodiazapines include, for example, lorazepam. Side effects of the benzodiazapines include perceptual disturbances, urinary incontinence, hypotension, diarrhea, sedation and amnesia.

Corticosteroids such as dexamethasone and methylprednisolone are useful in combination therapy, but shown little efficacy as a single agent. Side effects include, hyperglycemia, euphoria, insomnia and rectal pain.

The antiemetic property of tricyclic antidepressants has been assessed on a limited basis (see, e.g., Prakash et al., *Dig. Dis. Sci.* 43(9):1951–1956 (1998)) and cyclic vomiting syndrome (Prakash and Clouse,*Am. J. Gastroenterol.*, 94(10): 2855–2860 (1999).

However, the undesirable side effects associated with the use of tricyclic antidepressants are a significant drawback for this therapy. For example, the anticholinergic properties of the tricyclic antidepressants can cause dry mouth, constipation, blurred vision, urinary retention, weight gain, hypertension and cardiac side effects, such as palpitations and arrhythmia.

Antagonism of the 5-HT$_3$ receptor has been the focus of antiemetic therapy. More specifically, 5-HT$_3$ receptors are widely distributed in the mammalian central, peripheral and enteric nervous systems. The enteric nervous system resides within the walls of the gastrointestinal tract. 5-HT$_3$ receptors have been found to play an important role in the control of vomiting in a variety of mammals including humans (Veyrat-Follet et al., *Drugs* 53(2):206–234 (1997)). The receptors are present in the part of the brain that is involved in controlling vomiting as well as in the gastrointestinal tract. Receptors at both locations have been shown to be involved in vomiting. It is thought that 5-HT released from the enterochromaffin cells of the gastrointestinal mucosa acts on 5-HT$_3$ receptors to initiate the vomiting reflex. Chemotherapy and radiotherapy, two important clinical causes of vomiting, can cause release of 5-HT from the enterochromaffin cells. Chemotherapeutic agents also appear to act directly on the chemoreceptor trigger zone (CTZ) of the vomiting center in the brain that then feeds onto neurons containing 5-HT$_3$ receptors to initiate vomiting. That is, activation of the chemoreceptor trigger zone (CTZ) triggers the release of neurotransmitters that activate the vomiting center. CTZ neurotransmitters that are thought to cause emesis include, but are not limited to, dopamine, serotonin, histamine and norepinephrine.

However, improved treatment regimens are still needed. For example, the use of 5-HT$_3$ receptor antagonists such as ondansetron, granisetron and tropisetron has been shown to be less effective for delayed nausea and vomiting than for acute symptoms. In addition, efficacy of the 5-HT$_3$ receptor antagonists appears to be less pronounced for moderate emetogenic chemotherapy regimens than for cisplatin-containing regimens. Further, control over nausea appears to be significantly less than control over vomiting. Further, the efficacy of the agents appears to diminish across repeated days and across repeated chemotherapy cycles (see, e.g., Morrow et al., *Cancer* 76(3): 343–357 (1995)).

As such, improved methods for the treatment of vomiting, nausea, retcning or any combination thereof are needed.

SUMMARY OF THE INVENTION

The invention relates to a method of treating nausea, vomiting, retching or any combination thereof in a subject in need of treatment. The method comprises administering to a subject in need of treatment a therapeutically effective amount of a compound that has 5-HT3 receptor antagonist activity and NorAdrenaline Reuptake Inhibitor (NARI) activity.

In a particular embodiment, the compounds having 5-HT$_3$ receptor antagonist activity and NARI activity are thieno[2,3-d]pyrimidine derivatives such as those described in U.S. Pat. No. 4,695,568, the entire content of which is incorporated herein by reference.

In a specific embodiment, the compounds having 5-HT$_3$ receptor antagonist activity and NARI activity are represented by structural Formula I:

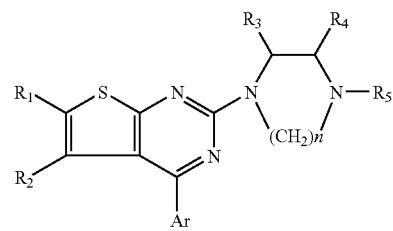

I wherein, $R_1$, and $R_2$ independently represent hydrogen, halogen or a $C_1$–$C_6$ alkyl group; or $R_1$, and $R_2$ together with the carbon atoms to which they are attached form a cycloalkylene group having 5 to 6 carbon atoms;

$R_3$ and $R_4$ independently represent hydrogen or a $C_1$–$C_6$ alkyl group;

$R_5$ is hydrogen, $C_1$–$C_6$ alkyl,

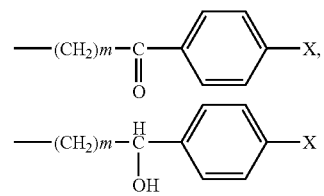

or —C(O)—NH—$R_6$, wherein m is an integer from about 1 to about 3, X is halogen and $R_6$ is a $C_1$–$C_6$ alkyl group;

Ar is a substituted or unsubstituted phenyl, 2-thienyl or 3-thienyl group; and n is 2 or 3; or a pharmaceutically acceptable salt thereof.

In a specific embodiment, the compound having 5-HT$_3$ receptor antagonist activity and NARI activity is represented by the formula:

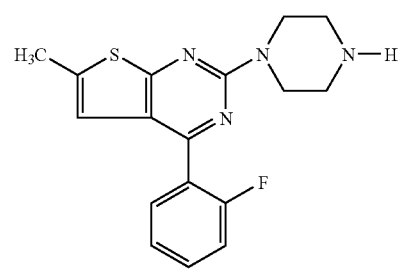

II or a pharmaceutically acceptable salt thereof. This compound is referred to as MCI-225 or DDP-225. The chemical name of the structure set forth in the formula is: 4-(2-fluorophenyl)-6-methyl-2-(1-piperazinyl)thieno[2,3-d]pyrimidine.

In one embodiment, the nausea, vomiting, retching or any combination thereof can be caused by anesthetics, radiation, cancer chemotherapeutic agents, toxic agents, odors, medicines, pregnancy and motion.

In a particular embodiment, the nausea, vomiting, retching or any combination thereof can be caused by administration of general anesthetics associated with surgical procedures.

In a more particular embodiment, the nausea, vomiting, retching or any combination thereof can be caused by administration of chemotherapeutic agents, radiation therapy or a combination thereof.

In yet another embodiment, the nausea, vomiting, retching or any combination thereof can be caused by conditions which are associated with vertigo. For example, the nausea, vomiting, retching or any combination thereof can be caused by Meniere's disease or vestibular neuronitis.

In another embodiment, the nausea, vomiting, retching or any combination thereof can be caused by headache. In particular embodiments, the headache is a result of migraine, increased intracranial pressure or cerebral vascular hemorrhage.

In yet another embodiment, the nausea, vomiting, retching or any combination thereof can be caused by maladies of the gastrointestinal (GI) tract. In a particular embodiment, the malady of the gastrointestinal tract is selected from the group consisting of cholecystitis, choledocholithiasis, intestinal obstruction, acute gastroenteritis, perforated viscus, dyspepsia and Zollinger-Ellison syndrome.

In a further embodiment, the vomiting, nausea, retching or any combination thereof, can be of undetermined etiology. In a particular embodiment, the nausea, vomiting, retching or any combination thereof can be characterized as Cyclic Vomiting Syndrome.

The invention further relates to a method of treating nausea, vomiting, retching or any combination thereof in a subject in need thereof, comprising coadministering to said subject a therapeutically effective amount of a 5-HT$_3$ receptor antagonist and a therapeutically effective amount of a NARI.

The invention further relates to a method of treating nausea, vomiting, retching or any combination thereof in a subject in need thereof, comprising coadministering to said subject a first amount of a 5-HT$_3$ receptor antagonist and a second amount of a NARI, wherein the first and second amounts together comprise a therapeutically effective amount.

In one embodiment, the coadministration can be used to treat nausea, vomiting, retching or any combination thereof caused by anesthetics, radiation, cancer chemotherapeutic agents, toxic agents, odors, medicines, pregnancy and motion.

In a particular embodiment, the coadministration can be used to treat nausea, vomiting, retching or any combination thereof caused by administration of general anesthetics associated with surgical procedures.

In a more particular embodiment, the coadministration can be used to treat nausea, vomiting, retching or any combination thereof caused by administration of chemotherapeutic agents, radiation therapy or a combination thereof.

In yet another embodiment, the coadministration can be used to treat nausea, vomiting, retching or any combination thereof caused by conditions which are associated with vertigo. For example, the nausea, vomiting, retching or any combination thereof can be caused by Meniere's disease or vestibular neuronitis.

In another embodiment, the coadministration can be used to treat nausea, vomiting, retching or any combination thereof caused by headache. In particular embodiments, the headache is a result of migraine, increased intracranial pressure or cerebral vascular hemorrhage.

In yet another embodiment, the coadministration can be used to treat nausea, vomiting, retching or any combination thereof caused by maladies of the gastrointestinal (GI) tract. In a particular embodiment, the malady of the gastrointestinal tract is selected from the group consisting of cholecystitis, choledocholithiasis, intestinal obstruction, acute gastroenteritis, perforated viscus, dyspepsia and Zollinger-Ellison syndrome.

In a further embodiment, the coadministration can be used to treat vomiting, nausea, retching or any combination thereof, of undetermined etiology. In a particular embodiment, the nausea, vomiting, retching or any combination thereof can be characterized as Cyclic Vomiting Syndrome.

In addition, the invention relates to a method of treating nausea, vomiting, retching or any combination thereof in a subject in need thereof comprising administering a therapeutically effective amount of a NARI. In this embodiment, the NARI is characterized by the substantial absence of anticholinergic effects.

In one embodiment, the nausea, vomiting, retching or any combination thereof can be caused by anesthetics, radiation, cancer chemotherapeutic agents, toxic agents, odors, medicines, pregnancy and motion.

In a particular embodiment, the nausea, vomiting, retching or any combination thereof can be caused by administration of general anesthetics associated with surgical procedures.

In a more particular embodiment, the nausea, vomiting, retching or any combination thereof can be caused by administration of chemotherapeutic agents, radiation therapy or a combination thereof.

In yet another embodiment, the nausea, vomiting, retching or any combination thereof can be caused by conditions which are associated with vertigo. For example, the nausea, vomiting, retching or any combination thereof can be caused by Meniere's disease or vestibular neuronitis.

In another embodiment, the nausea, vomiting, retching or any combination thereof can be caused by headache. In particular embodiments, the headache is a result of migraine, increased intracranial pressure or cerebral vascular hemorrhage.

In yet another embodiment, the nausea, vomiting, retching or any combination thereof can be caused by maladies of the gastrointestinal (GI) tract. In a particular embodiment, the malady of the gastrointestinal tract can be selected from the group consisting of cholecystitis, choledocholithiasis, intestinal obstruction, acute gastroenteritis, perforated viscus, dyspepsia and Zollinger-Ellison syndrome.

In a further embodiment, the vomiting, nausea, retching or any combination thereof, can be of undetermined etiology. In a particular embodiment, the nausea, vomiting, retching or any combination thereof can be characterized as Cyclic Vomiting Syndrome.

The invention further relates to pharmaceutical compositions useful for the treatment of a nausea, vomiting, retching or any combination thereof. The pharmaceutical composition comprises a first amount of a 5-HT$_3$ receptor antagonist compound and a second amount of a NARI compound. The pharmaceutical compositions of the present invention can optionally contain a pharmaceutically acceptable carrier. The 5-HT$_3$ receptor antagonist and the NARI can each be present in the pharmaceutical composition in a therapeutically effective amount. In another aspect, said first and second amounts can together comprise a therapeutically effective amount.

The pharmaceutical composition can be used to treat vomiting, nausea, retching or combinations thereof caused by a number of factors including, but not limited to, anesthetics, radiation, cancer chemotherapeutic agents, toxic agents, odors, medicines, for example, serotonin reuptake inhibitors, analgesics such as morphine, antibiotics and antiparasitic agents, pregnancy and motion. Conditions which are associated with vertigo (e.g., Meniere's disease and vestibular neuronitis) can also cause nausea, vomiting, retching or any combination thereof. Headache, caused by, for example, migraine, increased intracranial pressure or cerebral vascular hemorrhage can also result in nausea, vomiting, retching or any combination thereof. In addition, certain maladies of the gastrointestinal (GI) tract, for example, cholecystitis, choledocholithiasis, intestinal obstruction, acute gastroenteritis, perforated viscus, dyspepsia resulting from, for example, gastroesophageal reflux disease, peptic ulcer disease, gastroparesis, gastric or esophageal neoplasms, infiltrative gastric disorders (e.g., Menetrier's syndrome, Crohn's disease, eosinophilic gastroenteritis, sarcoidosis and amyloidosis) gastric infections (e.g., CMV, fuingal, TB and syphilis), parasites (e.g., *Giardia lamblia* and *Strongyloides stercoralis*), chronic gastric volvulus, chronic intestinal ischemia, altered gastric motility and/or food intolerance or Zollinger-Ellison syndrome can result in vomiting, nausea, retching or any combination thereof.

The invention further relates to use of a compound that has 5-HT$_3$ receptor antagonist activity and NARI activity for the manufacture of a medicament for treating nausea, vomiting, retching or any combination thereof In addition, the invention also relates to the use of a pharmaceutical composition comprising a first amount of a 5-HT$_3$ receptor antagonist compound and a second amount of a NARI compound for the manufacture of a medicament for the treatment of a nausea, vomiting, retching or any combination thereof. The pharmaceutical composition used for the manufacture of a medicament for treating nausea, vomiting, retching or any combination thereof can optionally contain a pharmaceutically acceptable carrier. The 5-HT$_3$ receptor antagonist and the NARI can each be present in the pharmaceutical composition in a therapeutically effective amount or said first and second amounts can together comprise a therapeutically effective amount. Further, the invention relates to the use of a NARI for the manufacture of a medicament for treating nausea, vomiting, retching or any combination thereof.

The foregoing and other objects, features and advantages of the invention will be apparent from the following more particular description of preferred embodiments of the invention.

DETAILED DESCRIPTION OF THE INVENTION

Figure 1:
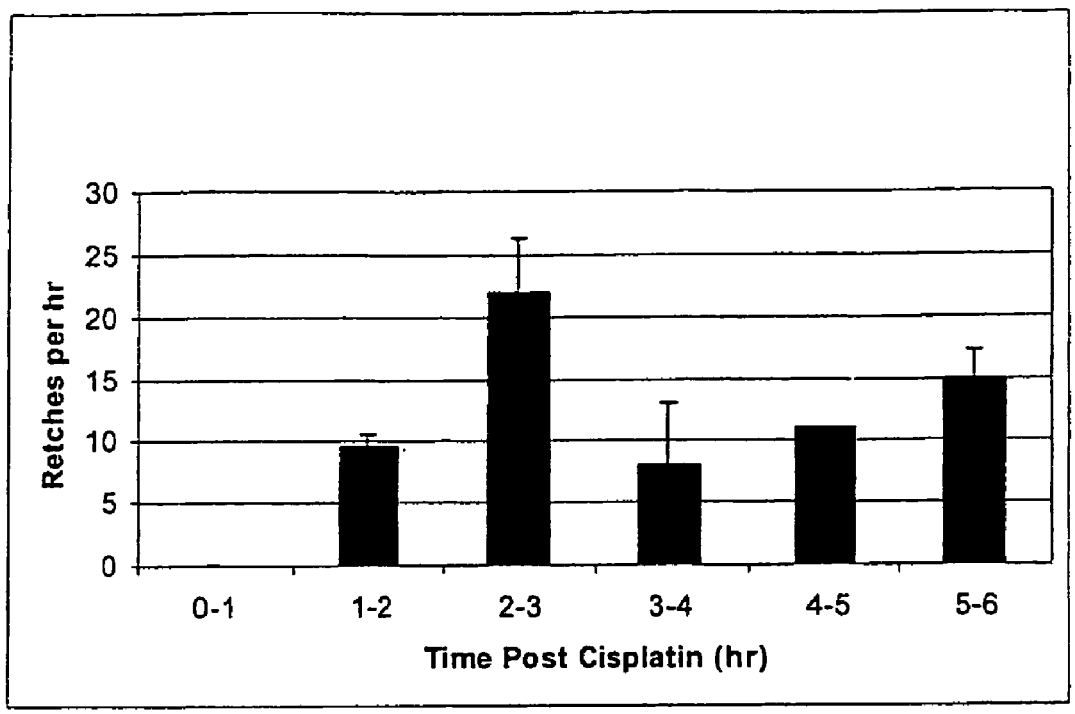
FIG. 1 is a bar graph of cisplatin-induced retches per hour versus time (hours) post administration of cisplatin in male ferrets treated with a 5 mg/kg dose of cisplatin and vehicle.

The invention relates to methods of treating nausea, vomiting, retching or any combination thereof.

Monoamine Neurotransmitters:

Monoamine neurotransmitters such as noradrenaline (also referred to as norepinephrine), serotonin (5-hydroxytryptamine, 5-HT) and dopamine are known and disturbances in these neurotransmitters have been indicated in many types of disorders, such as depression. These neurotransmitters travel from the terminal of a neuron across a small gap referred to as the synaptic cleft and bind to receptor molecules on the surface of a second neuron. This binding elicits intracellular changes that initiate or activate a response or change in the postsynaptic neuron. Inactivation occurs primarily by transport of the neurotransmitter back into the presynaptic neuron, which is referred to as reuptake. These neurons can be found both in the Central Nervous System (CNS) and in the Enteric Nervous System (ENS).

Noradrenaline and Noradrenaline Reuptake Inhibitors:

As used herein, the term NorAdrenaline Reuptake Inhibitor (NARI) refers to an agent (e.g., a molecule, a compound) which can inhibit noradrenaline transporter function. For example, a NARI can inhibit binding of a ligand of a noradrenaline transporter to said transporter and/or inhibit transport (e.g., uptake or reuptake of noradrenaline). As such, inhibition of the noradrenaline transport function in a subject, can result in an increase in the concentration of physiologically active noradrenaline. It is understood that NorAdrenergic Reuptake Inhibitor and NorEpinephrine Reuptake Inhibitor (NERI) are synonymous with NorAdrenaline Reuptake Inhibitor (NARI).

As used herein, noradrenaline transporter refers to naturally occurring noradrenaline transporters (e.g., mammalian noradrenaline transporters (e.g., human (*Homo sapiens*) noradrenaline transporters, murine (e.g., rat, mouse) noradrenaline transporters)) and to proteins having an amino acid sequence which is the same as that of a corresponding naturally occurring noradrenaline transporter (e.g., recombinant proteins). The term includes naturally occurring variants, such as polymorphic or allelic variants and splice variants.

In certain embodiments, the NARI can inhibit the binding of a ligand (e.g., a natural ligand such as noradrenaline, or other ligand such as nisoxetine) to a noradrenaline transporter. In other embodiments, the NARI can bind to a noradrenaline transporter. For example, in a preferred embodiment, the NARI can bind to a noradrenaline transporter, thereby inhibiting binding of a ligand to said transporter and inhibiting transport of said ligand. In another preferred embodiment, the NARI can bind to a noradrenaline transporter, and thereby inhibit transport.

The NARI activity of a compound can be determined employing suitable assays. More specifically, to determine the inhibition constant (Ki) for noradrenaline reuptake, an assay which monitors inhibition of noradrenaline (NA) uptake can be used. For example, radiolabelled noradrenaline, such as [$^3$H]NA and the test compound of interest can be incubated under conditions suitable for uptake with brain tissue or a suitable fraction thereof, for example, a synaptosomal fraction from rat brain tissue (harvested and isolated in accordance with generally accepted techniques), and the amount of uptake of [$^3$H]NA in the tissue or fraction can be determined (e.g., by liquid scintillation spectrometry). $IC_{50}$ values can be calculated by nonlinear regression analysis. The inhibition constants, Ki values, can then be calculated from the $IC_{50}$ values using the Cheng-Prusoff equation:

$$K_i = \frac{IC_{50}}{1+([L]/K_d)}$$

wherein [L]=the concentration of free radioligand used in the assay and $K_d$=the equilibrium dissociation constant of the radioligand. To determine the non-specific uptake, incubations can be performed by following the same assay, but in the absence of test compound at 4° C. (i.e., under conditions not suitable for uptake).

In a preferred embodiment, NARI activity is determined using the radioligand uptake assay described above, according to the procedure detailed in Eguchi et al., *Arzneim.-Forschung/Drug Res.*, 47(12): 1337–47 (1997).

Specifically, rats are decapitated and the cortical, hypothalamic, hippocampal and striatal tissues are rapidly dissected. The tissues are homogenized (Potter homogenizer with Teflon pestle) in 10 volumes of ice cold 0.32 mol/L sucrose. The $P_2$ fraction is obtained by centrifugation at 1000×g for 10 minutes and 11500×g for 20 minutes and suspended in Krebs-Ringer phosphate buffer, pH 7.4 (124 mmol/L NaCl, 5 mmol/L KCl, 20 mmol/L $Na_2HPO_4$, 1.2 mmol/L $KH_2PO_4$, 1.3 mmol/L $MgSO_4$, 0.75 mmol/L $CaCl_2$, 10 mmol/L glucose). The [$^3$H]NA uptake assays are performed on the cortical and hypothalamic synaptosomes.

The assay tubes contain radiolabed noradrenaline, [$^3$H]NA, in a volume of 0.2 mL, compounds at 5 or more concentrations in a volume of 0.1 mL, and the oxygenated buffer described above in a volume of 0.5 mL. After 5 minutes preincubation at 37° C., uptake is initiated by the addition of the synaptosomal fraction in volume of 0.2 mL. The final concentration of [$^3$H]NA in the incubation mixtures is 0.25 μmol/L. The reaction is stopped after 5 minutes by filtration through Whatman GF/B glass fiber filter under a vacuum with a cell harvester. The filter is rinsed three times with 4 mL of saline and placed in a scintillation vial containing 10 mL of Atomlight (Du Pont/NEN Research Products). Radioactivity is measured by liquid scintillation spectrometry. For determination of non-specific uptake, incubations are performed at 4° C. without the addition of test compounds. $IC_{50}$ values are calculated by nonlinear regression analysis. Inhibitor constants, Ki values, are calculated from the $IC_{50}$ values using the Cheng-Prusoff equation.

NARI compounds suitable for use in the invention have a Ki value for NARI activity of about 500 nmol/L or less, such as about 250 nmol/L or less, for example, about 100 nmol/L or less. It is preferred that the Ki value for NARI activity be about 100 nmol/L or less. It is understood that the exact value of the Ki for a particular compound can vary depending on the assay conditions employed for determination (e.g., radioligand and tissue source). As such, it is preferred that the NARI activity be assessed essentially according to the radioligand binding assay described in Eguchi et al., *Arzneim.-Forschung/Drug Res.*, 47(12): 1337–47 (1997) and discussed in detail above.

In addition, to possessing sufficient NARI activity, it is preferred that the NARI compounds possess one or more characteristics selected from the group consisting of:
a. the substantial absence of anticholinergic effects;
b. the selective inhibition of noradrenaline reuptake as compared to inhibition of serotonin reuptake; and
c. the selective inhibition of noradrenaline reuptake as compared to inhibition of dopamine reuptake.

Selective inhibition of noradrenaline reuptake as compared to inhibition of serotonin or dopamine reuptake can be determined by comparing the Ki values for the respective reuptake inhibitions. The inhibition constants for serotonin and dopamine reuptake can be determined as described above for nordrenaline, but employing the appropriate radioligand and tissue for the activity being assessed (e.g., [$^3$H] 5-HT for serotonin, using e.g., hypothalarnic or cortical tissue and [$^3$H]DA for dopamine (DA), using e.g., striatal tissue).

A preferred method of determining serotonin reuptake inhibition and dopaminergic reuptake inhibition is described in Eguchi et al., *Arzneim.-Forschung/Drug Res.*, 47(12): 1337–47 (1997). Specifically, rats are decapitated and the cortical, hypothalamic, hippocampal and striatal tissues are rapidly dissected. The tissues are homogenized (Potter homogenizer with Teflon pestle) in 10 volumes of ice cold 0.32 mol/L sucrose. The $P_2$ fraction is obtained by centrifugation at 1000×g for 10 minutes and 11500×g for 20 minutes and suspended in Krebs-Ringer phosphate buffer, pH 7.4 (124 mmol/L NaCl, 5 mmol/L KCl, 20 mmol/L $Na_2HPO_4$, 1.2 mmol/L $KH_2PO_4$, 1.3 mmol/L $MgSO_4$, 0.75 mmol/L $CaCl_2$, 10 mmol/L glucose). The [$^3$H]5-HT uptake assays are performed on the cortical, hypothalamic and hippocampal synaptosomes, and the [$^3$H]DA uptake assays are performed on striatal synaptosomes.

The assay tubes contain the appropriate radiolabled ligand (i.e., [$^3$H]5-HT or [$^3$H]DA), in a volume of 0.2 mL, compounds at 5 or more concentrations in a volume of 0.1 mL, and the oxygenated buffer described above in a volume of 0.5 mL. After 5 minutes preincubation at 37° C., uptake is initiated by the addition of the synaptosomal fraction in volume of 0.2 mL. The final concentration of [$^3$H]DA in the striatal incubation mixtures is 0.4 μmol/L. The final concentrations of [$^3$H]5-HT in the cortical, hypothalamic and hippocampal synaptosome incubation mixtures are 0.02 μmol/L, 0.04 μmol/L and 0.08 μmol/L. The reaction is stopped after 5 minutes ([$^3$H]5-HT) or 3 minutes [$^3$H]DA by filtration through Whatman GF/B glass fiber filter under a vacuum with a cell harvester. The filter is rinsed three times with 4 mL of saline and placed in a scintillation vial containing 10 mL of Atomlight (Du Pont/NEN Research Products). Radioactivity is measured by liquid scintillation spectrometry. For determination of non-specific uptake incubations are performed at 4° C. without the addition of test compounds. $IC_{50}$ values are calculated by nonlinear regression analysis. Inhibition constants, Ki values, are calculated from the $IC_{50}$ values using the Cheng-Prusoff equation.

Following determination of the Ki values for inhibition of noradrenaline, serotonin and/or dopamine uptake, the ratio of the activities can be determined. Selective inhibition of noradrenaline reuptake as compared to inhibition of serotonin reuptake and/or dopaminergic reuptake, refers to a compound having a Ki value for inhibition of serotonin (re)uptake and/or dopamine (re)uptake which is about 10 times or more than the Ki for inhibition of noradrenaline (re)uptake. That is, the ratio, Ki inhibition of serotonin (re)uptake/Ki inhibition of noradrenaline (re)uptake, is about 10 or more, such as about 15 or more, about 20 or more, for example, about 30, 40 or 50 or more. Likewise, the ratio, Ki inhibition of dopamine (re)uptake/Ki inhibition noradrenaline (re)uptake, is about 10 or more, such as about 15 or more, about 20 or more, for example, about 30, 40 or 50 or more.

It is preferred that the Ki values for comparison are determined according to the method of Eguchi et al., discussed in detail above. It is most preferred, that the Ki values for NARI activity and inhibition of serotonin reuptake activity, which are compared to determine selective inhibition are determined according to the method of Eguchi et al. using a synaptosomal preparation from rat hypothalamic tissue. Further, it is most preferred, that the Ki values for NARI activity and inhibition of dopamine reuptake activity, which are compared to determine selective inhibition are determined according to the method of Eguchi et al. using a synaptosomal preparation from rat hypothalamic tissue for inhibition of noradrenaline uptake and from rat striatal tissue for inhibition of dopamine uptake.

In another embodiment, the NARI is characterized by the substantial absence of anticholinergic effects. As used herein, substantial absence of anticholinergic effects, refers to a compound which has an $IC_{50}$ value for binding to muscarinic receptors of about 1 µmol/L or more. The $IC_{50}$ value for binding to muscarinic receptors can be determined using a suitable assay, such as an assay which determines the ability of a compound to inhibit the binding of suitable radioligand to muscarinic receptors. A preferred assay for determination of the $IC_{50}$ value for binding of a compound to muscarinic receptors is described in Eguchi et al., Arzneim.-Forschung/Drug Res., 47(12): 1337–47 (1997).

Specifically, the binding assays for determination of binding to muscarinic receptors can be performed on tissue isolated from the rat cerebral cortex. The buffer is any suitable buffer, for example, 50 mmol/L Tris-HCl, pH=7.4. The preferred radiolabeled ligand is [$^3$H]QNB (3-quinuclidinyl benzilate) which is present in a final concentration of 0.2 nmol/L. The test compound is added at various concentrations and the resulting mixtures are incubated for 60 minutes at 37° C. The reaction is terminated by rapid vacuum filtration onto glass fiber filter. Radioactivity trapped on the filter is measured by scintillation spectrometry. Non-specific binding is determined using 100 µmol/L atropine. $IC_{50}$ values can be calculated by nonlinear regression analysis.

In a particular embodiment, the NARI compound can be selected from venlafaxine, duloxetine, buproprion, milnacipran, reboxetine, lefepramine, desipramine, nortriptyline, tomoxetine, maprotiline, oxaprotiline, levoprotiline, viloxazine and atomoxetine.

In a preferred embodiment, the NARI compound can be selected from reboxetine, lefepramine, desipramine, nortriptyline, tomoxetine, maprotiline, oxaprotiline, levoprotiline, viloxazine and atomoxetine.

Setotonin and 5-HT$_3$ Receptor Antagonists:

The neurotransmitter serotonin was first discovered in 1948 and has subsequently been the subject of substantial scientific research. Serotonin, also referred to as 5-hydroxytryptamine (5-HT), acts both centrally and peripherally on discrete 5-HT receptors. Currently, fourteen subtypes of serotonin receptors are recognized and delineated into seven families, 5-HT, through 5-HT$_7$. These subtypes share sequence homology and display some similarities in their specificity for particular ligands. A review of the nomenclature and classification of the 5-HT receptors can be found in Neuropharn., 33: 261–273 (1994) and Pharm. Rev., 46:157–203 (1994).

5-HT$_3$ receptors are ligand-gated ion channels that are extensively distributed on enteric neurons in the human gastrointestinal tract, as well as other peripheral and central locations. Activation of these channels and the resulting neuronal depolarization have been found to affect the regulation of visceral pain, colonic transit and gastrointestinal secretions. Antagonism of the 5-HT$_3$ receptors has the potential to influence sensory and motor function in the gut.

As used herein, 5-HT$_3$ receptor refers to naturally occurring 5-HT$_3$ receptors (e.g., mammalian 5-HT$_3$ receptors (e.g., human (Homo sapiens) 5-HT$_3$ receptors, murine (e.g., rat, mouse) 5-HT$_3$ receptors)) and to proteins having an amino acid sequence which is the same as that of a corresponding naturally occurring 5-HT$_3$ receptor (e.g., recombinant proteins). The term includes naturally occurring variants, such as polymorphic or allelic variants and splice variants.

As used herein, the term 5-HT$_3$ receptor antagonist refers to an agent (e.g., a molecule, a compound) which can inhibit 5-HT$_3$ receptor function. For example, a 5-HT$_3$ receptor antagonist can inhibit binding of a ligand of a 5-HT$_3$ receptor to said receptor and/or inhibit a 5-HT$_3$ receptor-mediated response (e.g., reduce the ability of 5-HT$_3$ to evoke the von Bezold-Jarisch reflex).

In certain embodiments, the 5-HT$_3$ receptor antagonist can inhibit binding of a ligand (e.g., a natural ligand, such as serotonin (5-HT$_3$), or other ligand such as GR65630) to a 5-HT$_3$ receptor. In certain embodiments, the 5-HT$_3$ receptor antagonist can bind to a 5-HT$_3$ receptor. For example, in a preferred embodiment, the 5-HT$_3$ receptor antagonist can bind to a 5-HT$_3$ receptor, thereby inhibiting the binding of a ligand to said receptor and a 5-HT$_3$ receptor-mediated response to ligand binding. In another preferred embodiment, the 5-HT$_3$ receptor antagonist can bind to a 5-HT$_3$ receptor, and thereby inhibit a 5-HT$_3$ receptor-mediated response.

5-HT$_3$ receptor antagonists can be identified and activity assessed by any suitable method, for example, by a method which assesses the ability of a compound to inhibit radioligand binding to 5-HT$_3$ receptor (see, for example, Eguchi et al., Arzneim.-Forschung/DrugRes., 47(12): 1337–47 (1997) and G. Kilpatrick et al., Nature, 330: 746–748 (1987)) and/or by their effect on the 5-HT$_3$-induced von Bezold-Jarisch (B-J) reflex in the cat or rat (following the general methods described by Butler et al., Br. J. Pharmacol., 94: 397–412 (1988) and Ito et al., J. Pharmacol. Exp. Ther., 280(1): 67–72 (1997), respectively).

In a preferred embodiment, 5-HT$_3$ receptor antagonist activity of a compound can be determined according to the method described in Eguchi et al., *Arzneim.-Forschung/ Drug Res.*, 47(12): 1337–47 (1997). Specifically, the binding assays for determination of binding to the 5-HT$_3$ receptor can be performed on N1E-115 mouse neuroblastoma cells (American Type Culture Collection (ATCC) Accession No. CRL-2263) in 20 mmol/L HEPES buffer (pH=7.4) containing 150 mmol/L NaCl, 0.35 mmol/L of radiolabeled ligand ([$^3$H]GR65630) and the test compound at 6 or more concentrations at 25° C. for 60 minutes. The reaction is terminated by rapid vacuum filtration onto glass fiber filter. Radioactivity trapped on the filter is measured by scintillation spectrometry. Non-specific binding is determined using 1 μmol/L of MDL-7222 (endo-8-methyl-8-azabicyclo [3.2.1]oct-3-yl-3,5-dichlorobenzoate. IC$_{50}$ values are calculated by nonlinear regression analysis. The affinity constants, Ki values, are calculated from the IC$_{50}$ values using the Cheng-Prusoff equation.

Compounds having 5-HT$_3$ receptor antagonist activity which are suitable for use in the invention have an affinity for 5-HT$_3$ receptor (Ki) of not more than about 250 times the Ki of ondansetron for 5-HT$_3$ receptor. This relative activity to ondansetron (Ki of test agent for 5-HT$_3$ receptor/Ki of ondansetron for 5-HT$_3$ receptor), can be determined by assaying the compound of interest and ondansetron using a suitable assay under controlled conditions, for example, conditions which differ primarily in the agent being tested. It is preferred that the relative activity of the 5-HT$_3$ receptor antagonist activity be not more than about 200 times that of ondansetron, for example, not more than about 150 times that of ondansetron, such as not more than about 100 times that of ondansetron, for example, not more than about 50 times that of ondansetron. In a particularly preferred embodiment, the compound having 5-HT$_3$ receptor antagonist activity has a relative activity to ondansetron of not more than about 10.

In certain embodiments, the 5-HT$_3$ receptor antagonist can be selected from indisetron, YM-114 ((R)-2,3-dihydro-1-[(4,5,6,7-tetrahydro-1H-benzimidazol-5-yl-)carbonyl]-1H-indole), granisetron, talipexole, azasetron, bemesetron, tropisetron, ramosetron, ondansetron, palonosetron, lerisetron, alosetron, N-3389, zacopride, cilansetron, E-3620 ([3(S)-endo]-4-amino-5-chloro-N-(8-methyl-8-azabicyclo [3.2.1-]oct-3-yl-2[(1-methyl-2-butynyl)oxy]benzamide), lintopride, KAE-393, itasetron, zatosetron, dolasetron, (±)-zacopride, (±)-renzapride, (−)-YM-060, DAU-6236, BIMU-8 and GK-128 [2-[2-methylimidazol-1-yl)methyl]-benzo[f]thiochromen-1-one monohydrochloride hemihydrate].

In preferred embodiments, the 5-HT$_3$ receptor antagonist can be selected from indisetron, granisetron, azasetron, bemesetron, tropisetron, ramosetron, ondansetron, palonosetron, lerisetron, alosetron, cilansetron, itasetron, zatosetron, and dolasetron.

The invention relates to a method of treating nausea, vomiting, retching or any combination thereof in a subject in need of treatment. The method comprises administering to a subject in need of treatment a therapeutically effective amount of a compound that has 5-HT$_3$ receptor antagonist activity and NARI activity.

In a particular embodiment, the compounds having 5-HT$_3$ receptor antagonist activity and NARI activity are thieno[2,3-d]pyrimidine derivatives such as those described in U.S. Pat. No. 4,695,568, the entire content of which is incorporated herein by reference.

In a specific embodiment, the compounds having 5-HT$_3$ receptor antagonist activity and NARI activity are represented by Formula I:

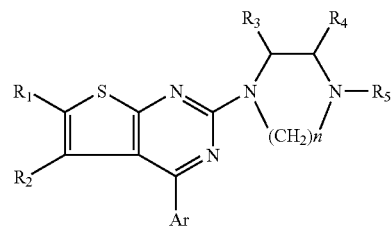

wherein, $R_1$ and $R_2$ independently represent hydrogen, halogen or a $C_1$–$C_6$ alkyl group; or $R_1$ and $R_2$ together with the carbon atoms to which they are attached form a cycloalkylene group having 5 to 6 carbon atoms;

$R_3$ and $R_4$ independently represent hydrogen or a $C_1$–$C_6$ alkyl group;

$R_5$ is hydrogen, $C_1$–$C_6$ alkyl,

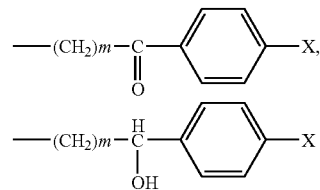

or —C(O)—NH—$R_6$,
wherein m is an integer from about 1 to about 3, X is halogen and $R_6$ is a $C_1$–$C_6$ alkyl group;

Ar is a substituted or unsubstituted phenyl, 2-thienyl or 3-thienyl group; and n is 2 or 3; or a pharmaceutically acceptable salt thereof.

Substituted phenyl, 2-thienyl or 3-thienyl group refers to a phenyl, 2-thienyl or 3-thienyl group in which at least one of the hydrogen atoms available for substitution has been replaced with a group other than hydrogen (i.e., a substituent group). Multiple substituent groups can be present on the phenyl, 2-thienyl or 3-thienyl ring. When multiple substituents are present, the substituents can be the same or different and substitution can be at any of the substitutable sites on the ring. Substituent groups can be, for example, a halogen atom (fluorine, chlorine, bromine or iodine); an alkyl group, for example, a $C_1$–$C_6$ alkyl group such as a methyl, ethyl, propyl, butyl, pentyl or hexyl group; an alkoxy group, for example, a $C_1$–$C_6$ alkoxy group such as methoxy, ethoxy, propoxy, butoxy; a hydroxy group; a nitro group; an amino group; a cyano group; or an alkyl substituted amino group such as methylamino, ethylamino, dimethylamino or diethylamino group.

Alkyl group refers to a straight chain or branched alkyl group. $C_1$–$C_6$ alkyl group refers to a straight-chain or branched alkyl group having from one to six carbon atoms. For example, the $C_1$–$C_6$ alkyl group can be a strain-chain alkyl such as methyl, ethyl, propyl, etc. Alternatively, the alkyl group can be branched for example, an isopropyl or t-butyl group.

Halogen refers to fluorine, chlorine, bromine or iodine.

In a particular embodiment, the compounds having 5-HT$_3$ receptor antagonist activity and NARI activity are represented by Formula I, wherein $R_1$ is a $C_1$–$C_6$ alkyl group and Ar is a substituted phenyl. In this embodiment, it is preferred that the phenyl group is substituted with a halogen.

In a particularly preferred embodiment, the compounds having 5-HT$_3$ receptor antagonist activity and NARI activity are represented by Formula I, wherein n is 2, R$_1$ is a C$_1$–C$_6$ alkyl group and Ar is a substituted phenyl. Preferably, the phenyl group is substituted with a halogen and the alkyl group of R$_1$ is a methyl group.

In yet another embodiment, the compounds having 5-HT$_3$ receptor antagonist activity and NARI activity are represented by Formula I, wherein R$_1$ is a C$_1$–C$_6$ alkyl group or a halogen and Ar is an unsubstituted phenyl. Further, when R$_1$ is an alkyl group and Ar is an unsubstituted phenyl, R$_2$ can also be a hydrogen or a C$_1$–C$_6$ alkyl group.

In a particularly preferred embodiment, the compounds having 5-HT$_3$ receptor antagonist activity and NARI activity are represented by Formula I, wherein n is 2, R$_1$ is a C$_1$–C$_6$ alkyl group and Ar is an unsubstituted phenyl. In a specific embodiment, wherein n is 2, R$_1$ is a C$_1$–C$_6$ alkyl group and Ar is an unsubstituted phenyl, R$_2$ can be hydrogen or a C$_1$–C$_6$ alkyl group.

In a particularly preferred embodiment, the compound having 5-HT$_3$ receptor antagonist activity and NARI activity is represented by structural Formula II:

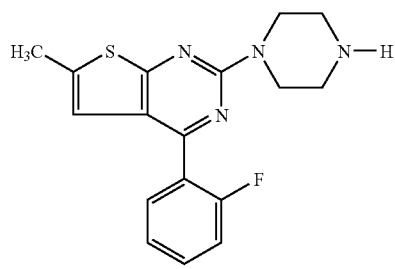

II or a pharmaceutically acceptable salt thereof. This compound is referred to as MCI-225 or DDP-225. The chemical name of the structure set forth in the formula is: 4-(2-fluorophenyl)-6-methyl-2-(1-piperazinyl)thieno[2,3-d]pyrimidine.

In another embodiment, the method further comprises administering a therapeutically effective amount of an (i.e., one or more) additional therapeutic agent.

Compounds having 5-HT$_3$ receptor antagonist activity and NARI activity, such as the compounds represented by structural Formulas I and II are useful for treating nausea, vomiting, retching or any combination thereof by virtue of the dual therapeutic modes of action which they can exhibit. That is, the unique ability to modulate the function of both the 5-HT$_3$ receptor and the noradrenaline reuptake mechanism can provide an enhanced treatment regimen for the subject undergoing treatment.

In a preferred embodiment, compounds having 5-HT$_3$ receptor antagonist activity and NARI activity, such as the compounds of Formula I and II possess one or more characteristics selected from the group consisting of:

a) the substantial absence of anticholinergic effects;
b) the selective inhibition of noradrenaline reuptake as compared to inhibition of serotonin reuptake; and
c) the selective inhibition of noradrenaline reuptake as compared to inhibition of dopamine reuptake.

For example, the specific compound MCI-225 has been shown to be a selective NARI and a 5-HT$_3$ receptor antagonist with substantially no anticholinergic activity. Eguchi et al., *Arzneim.-Forschung/DrugRes.*, 47(12): 1337–47 (1997), reported inhibition constants for MCI-225 for the uptake the [$^3$H]monoamine neurotransmitters noradrenaline, serotonin and dopamine in various rat brain tissues. More specifically, MCI-225 inhibited the uptake of [$^3$H]NA and [$^3$H]5-HT by synaptosomes from rat hypothalamic tissue with inhibition constants of Ki=35.0 nmol/L and Ki=491 nmol/L, respectively. In addition, MCI-225 inhibited the uptake of [$^3$H]NA and [$^3$H]5-HT by synaptosomes from rat cortical tissue with inhibition constants of Ki=0.696 nmol/L and Ki=1070 nmol/L, respectively. MCI-225 was also reported to inhibit the uptake of serotonin by synaptosomes from rat hippocampal tissue with an inhibition constant of Ki=244 nmol/L. Further, the MCI-225 inhibition constant for the uptake of [$^3$H]DA by synaptosomes from rat striatal tissue was reported as Ki=14,800. MCI-225 did not inhibit Monoamine Oxidase-A (MAO-A) and Monoamine Oxidase-B (MAO-B) activities.

With regard to 5-HT$_3$ receptor antagonist activity, Eguchi et al. reported that MCI-225 showed high affinity for the 5-HT$_3$ receptor (Ki less than 100 nmol/L) in comparison to the other receptors tested. In addition, MCI-225 showed affinity for the 5-HT$_3$ receptor similar to that reported for ondansetron in the same radioligand binding assay. Briefly, the inhibition of radiolabeled ligand binding by MCI-225, using a suitable radioligand and tissue combination for the receptor of interest was determined. The receptors tested included, $\alpha_1$, $\alpha_2$, $\beta_1$, $\beta_2$, 5-HT$_1$, 5-HT$_{1A}$, 5-HT$_{1c}$, 5-HT$_2$, 5-HT$_3$, 5-HT$_4$, 5-HT$_6$, 5-HT$_7$, D$_1$, D$_2$, Muscarinic, M$_1$, M$_2$, M$_3$, Nicotinic, H$_1$, H$_2$, GABA-A, GABA-B, BZP, Opiate non-selective, Opiate κ, Opiate μ, Opiate δ, CRF (Corticotropin Releasing Factor) and glucocorticoid. The IC$_{50}$ values determined for MCI-225, for these additional receptors were all greater than 1 μmol/L.

In one embodiment, the nausea, vomiting, retching or any combination thereof can be caused by anesthetics, radiation, cancer chemotherapeutic agents, toxic agents, odors, medicines, pregnancy and motion.

In a particular embodiment, the nausea, vomiting, retching or any combination thereof can be caused by administration of general anesthetics associated with surgical procedures.

In a more particular embodiment, the nausea, vomiting, retching or any combination thereof can be caused by administration of chemotherapeutic agents, radiation therapy or a combination thereof.

In yet another embodiment, the nausea, vomiting, retching or any combination thereof can be caused by conditions which are associated with vertigo. For example, the nausea, vomiting, retching or any combination thereof can be caused by Meniere's disease or vestibular neuronitis.

In another embodiment, the nausea, vomiting, retching or any combination thereof can be caused by headache. In particular embodiments, the headache can be a result of migraine, increased intracranial pressure or cerebral vascular hemorrhage.

In yet another embodiment, the nausea, vomiting, retching or any combination thereof can be caused by maladies of the gastrointestinal (GI) tract. In a particular embodiment, the malady of the gastrointestinal tract can be selected from the group consisting of cholecystitis, choledocholithiasis, intestinal obstruction, acute gastroenteritis, perforated viscus, dyspepsia and Zollinger-Ellison syndrome.

In a further embodiment, the vomiting, nausea, retching or any combination thereof, can be of undetermined etiology. In a particular embodiment, the nausea, vomiting, retching or any combination thereof can be characterized as Cyclic Vomiting Syndrome.

The invention further relates to a method of treating nausea, vomiting, retching or any combination thereof in a subject in need thereof, comprising coadministering to said subject a therapeutically effective amount of a 5-HT$_3$ receptor antagonist and a therapeutically effective amount of a NARI.

The invention further relates to a method of treating nausea, vomiting, retching or any combination thereof in a subject in need thereof, comprising coadministering to said subject a first amount of a 5-HT$_3$ receptor antagonist and a second amount of a NARL wherein the first and second amounts together comprise a therapeutically effective amount.

In one embodiment, the coadministration can be used to treat nausea, vomiting, retching or any combination thereof can be caused by anesthetics, radiation, cancer chemotherapeutic agents, toxic agents, odors, medicines, pregnancy and motion.

In a particular embodiment, the coadministration can be used to treat nausea, vomiting, retching or any combination thereof can be caused by administration of general anesthetics associated with surgical procedures.

In a more particular embodiment, the coadministration can be used to treat nausea, vomiting, retching or any combination thereof caused by administration of chemotherapeutic agents, radiation therapy or a combination thereof.

In yet another embodiment, the coadministration can be used to treat nausea, vomiting, retching or any combination thereof caused by conditions which are associated with vertigo. For example, the nausea, vomiting, retching or any combination thereof can be caused by Meniere's disease or vestibular neuronitis.

In another embodiment, the coadministration can be used to treat nausea, vomiting, retching or any combination thereof caused by headache. In particular embodiments, the headache is a result of migraine, increased intracranial pressure or cerebral vascular hemorrhage.

In yet another embodiment, the coadministration can be used to treat nausea, vomiting, retching or any combination thereof caused by maladies of the gastrointestinal (GI) tract. In a particular embodiment, the malady of the gastrointestinal tract is selected from the group consisting of cholecystitis, choledocholithiasis, intestinal obstruction, acute gastroenteritis, perforated viscus, dyspepsia and Zollinger-Ellison syndrome.

In a further embodiment, the coadministration can be used to treat vomiting, nausea, retching or any combination thereof, of undetermined etiology. In a particular embodiment, the nausea, vomiting, retching or any combination thereof can be characterized as Cyclic Vomiting Syndrome.

In another embodiment, the coadministration methods further comprise administering a therapeutically effective amount of an (i.e., one or more) additional therapeutic agent.

In certain embodiments of the coadministration method, the 5-HT$_3$ receptor antagonist can be selected from indisetron, YM-114 ((R)-2,3-dihydro-1-[(4,5,6,7-tetrahydro-1H-benzimidazol-5-yl-)carbonyl]-1H-indole), granisetron, talipexole, azasetron, bemesetron, tropisetron, ramosetron, ondansetron, palonosetron, lerisetron, alosetron, N-3389, zacopride, cilansetron, E-3620 ([3(S)-endo]-4-amino-5-chloro-N-(8-methyl-8-azabicyclo[3.2.1-]oct-3-yl-2[(1-methyl-2-butynyl)oxy]benzamide), lintopride, KAE-393, itasetron, zatosetron, dolasetron, (±)-zacopride, (±)-renzapride, (−)-YM-060, DAU-6236, BIMU-8 and GK-128 [2-[2-methylimidazol-1-yl)methyl]-benzo[f]thiochromen-1-one monohydrochloride hemihydrate].

In preferred embodiments, the 5-HT$_3$ receptor antagonist can be selected from indisetron, granisetron, azasetron, bemesetron, tropisetron, ramosetron, ondansetron, palonosetron, lerisetron, alosetron, cilansetron, itasetron, zatosetron, and dolasetron.

In certain embodiments, the NARI compound can be selected from venlafaxine, duloxetine, buprorion, milnacipran, reboxetine, lefepramine, desipramine, nortriptyline, tomoxetine, maprotiline, oxaprotiline, levoprotiline, viloxazine and atomoxetine.

In a preferred embodiment, the NARI compound can be selected from reboxetine, lefepramine, desipramine, nortriptyline, tomoxetine, maprotiline, oxaprotiline, levoprotiline, viloxazine and atomoxetine.

In a preferred embodiment, the NARI compound possesses one or more characteristics selected from the group consisting of:
  a) the substantial absence of anticholinergic effects;
  b) the selective inhibition of noradrenaline reuptake as compared to inhibition of serotonin reuptake; and
  c) the selective inhibition of noradrenaline reuptake as compared to inhibition of dopamine reuptake.

In addition, the invention relates to a method of treating nausea, vomiting, retching or any combination thereof in a subject in need thereof comprising administering a therapeutically effective amount of a NARI. In this embodiment, the NARI is characterized by the substantial absence of anticholinergic effects.

In a further embodiment, the NARI possesses selective inhibition of noradrenaline reuptake as compared to inhibition of serotonin reuptake and/or selective inhbition of noradrenaline reuptake as compared to inhibition of dopamine reuptake.

In one embodiment, the nausea, vomiting, retching or any combination thereof can be caused by anesthetics, radiation, cancer chemotherapeutic agents, toxic agents, odors, medicines, pregnancy and motion.

In a particular embodiment, the nausea, vomiting, retching or any combination thereof can be caused by administration of general anesthetics associated with surgical procedures.

In a more particular embodiment, the nausea, vomiting, retching or any combination thereof can be caused by administration of chemotherapeutic agents, radiation therapy or a combination thereof.

In yet another embodiment, the nausea, vomiting, retching or any combination thereof can be caused by conditions which are associated with vertigo. For example, the nausea, vomiting, retching or any combination thereof can be caused by Meniere's disease or vestibular neuronitis.

In another embodiment, the nausea, vomiting, retching or any combination thereof can be caused by headache. In particular embodiments, the headache can be a result of migraine, increased intracranial pressure or cerebral vascular hemorrhage.

In yet another embodiment, the nausea, vomiting, retching or any combination thereof can be caused by maladies of the gastrointestinal (GI) tract. In a particular embodiment, the malady of the gastrointestinal tract can be selected from the group consisting of cholecystitis, choledocholithiasis, intestinal obstruction, acute gastroenteritis, perforated viscus, dyspepsia and Zollinger-Ellison syndrome.

In a further embodiment, the vomiting, nausea, retching or any combination thereof, is of undetermined etiology. In a particular embodiment, the nausea, vomiting, retching or any combination thereof is Cyclic Vomiting Syndrome.

In another embodiment, the method further comprises administering a therapeutically effective amount of an (i.e., one or more) additional therapeutic agent. For example, the method can further comprise administering a corticosteroid.

The invention further relates to pharmaceutical compositions useful for the treatment of a nausea, vomiting, retching or any combination thereof. The pharmaceutical composition comprises a first amount of a 5-HT$_3$ receptor antagonist compound and a second amount of a NARI compound. The pharmaceutical compositions of the present invention can optionally contain a pharmaceutically acceptable carrier. The 5-HT$_3$ receptor antagonist and the NARI can each be present in the pharmaceutical composition in a therapeutically effective amount. In another aspect, said first and second amounts can together comprise a therapeutically effective amount.

In a further embodiment, the pharmaceutical composition further comprises an (i.e., one or more) additional therapeutic agent.

The pharmaceutical composition can be used in the treatment of a nausea, vomiting, retching or any combination thereof in a subject in need of treatment. As such, the invention relates to a method of treating nausea, vomiting, retching or any combination thereof in a subject in need of treatment comprising administering to the subject a therapeutically effective amount of a pharmaceutical composition as described herein.

An additional therapeutic agent suitable for use in the methods and pharmaceutical compositions described herein, can be, but is not limited to, for example: an anticholinergic (e.g., scopolomine); an antihistamine (e.g., dimenhydrinate and diphenhydramine); a phenothiazine (e.g., prochlorperazine and chlorpromazine); a butyrophenone (haloperidol and droperidol); a cannabinoid (e.g., tetrahydrocannabinol and nabilone); a benzamide (e.g., metoclopramide, cisapride and trimethobenzamide); a glucocorticoid (e.g., dexamethasone and methylprednisolone); a benzodiazepine (e.g., lorazepam); or any combination thereof In a preferred embodiment, the additional therapeutic agent is a glucocorticoid.

Vomiting, Nausea and Retching

Emesis and vomiting, as used herein, are synonymous and can be described as the forceful expulsion of gastrointestinal contents through the mouth brought about by the descent of the diaphragm and powerful contractions of the abdominal muscles. Emesis is usually, but not always, preceded by nausea.

Nausea, as used herein, is the unpleasant feeling that one is about to vomit.

Retching or dry heaves, as used herein, involves the same physiological mechanisms as vomiting, but occurs against a closed glottis, which prohibits the expulsion of gastric contents.

Nausea, vomiting, retching or combinations thereof can be caused by a number of factors including, but not limited to, anesthetics, radiation, cancer chemotherapeutic agents, toxic agents, odors, medicines, for example, serotonin reuptake inhibitors, analgesics such as morphine, antibiotics and antiparasitic agents, pregnancy and motion. Conditions which are associated with vertigo (e.g., Meniere's disease and vestibular neuronitis) can also cause nausea, vomiting, retching or any combination thereof. Headache, caused by, for example, migraine, increased intracranial pressure or cerebral vascular hemorrhage can also result in nausea, vomiting, retching or any combination thereof. In addition, certain maladies of the gastrointestinal (GI) tract, for example, cholecystitis, choledocholithiasis, intestinal obstruction, acute gastroenteritis, perforated viscus, dyspepsia resulting from, for example, gastroesophageal reflux disease, peptic ulcer disease, gastroparesis, gastric or esophageal neoplasms, infiltrative gastric disorders (e.g., Menetrier's syndrome, Crohn's disease, eosinophilic gastroenteritis, sarcoidosis and amyloidosis) gastric infections (e.g., CMV, fingal, TB and syphilis), parasites (e.g., *Giardia lamblia* and *Strongyloides stercoralis*), chronic gastric volvulus, chronic intestinal ischemia, altered gastric motility and/or food intolerance or Zollinger-Ellison syndrome can result in vomiting, nausea, retching or any combination thereof. However, in some cases of vomiting, nausea, retching or combinations thereof, no etiology can be determined despite extensive diagnostic testing(e.g., Cyclic Vomiting Syndrome).

Nausea, vomiting and retching are defined as acute when symptoms are present for less than a week. The causes of nausea, vomiting and retching of short duration are often separable from etiologies leading to more chronic symptoms.

Nausea, vomiting and retching are defined as chronic when symptoms are present for over a week. For example, symptoms can be continuous or intermittent and last for months or years.

Dyspepsia, as used herein, refers to pain or discomfort centered in the upper abdomen that can also include bloating, early satiety, postprandial fullness, nausea, anorexia, heartburn, regurgitation, and burping or belching. Generally, the symptoms of dyspepsia arise from the upper luminal GI tract. Dyspepsia can be caused by a number of foods, medications, systemic disorders and diseases of the luminal GI tract.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

As used herein, therapeutically effective amount refers to an amount sufficient to elicit the desired biological response. In the present invention the desired biological response is a reduction (complete or partial) in vomiting, nausea, retching or any combination thereof resulting from any cause.

Chemotherapeutic Agents

Chemotherapeutic agents, as that term is used herein, include, but are not limited to, for example alkylating agents, e.g. cyclophosphamide, carmustine, lomustine, and chlorambucil; cytotoxic antibiotics, e.g. dactinomycin, doxorubicin, mitomycin-C, and bleomycin; antimetabolites, e.g. cytarabine, methotrexate, and 5-fluorouracil; vinca alkaloids, e.g. etoposide, vinblastine, and vincristine; and others such as cisplatin, dacarbazine, procarbazine, and hydroxyurea; and combinations thereof Medicines In addition to chemotherapeutic agents, many other medicines can cause nausea, vomiting, retching or a combination thereof For example, analgesics, antibiotics, antiparasitic agents, and serotonin reuptake inhibitors can cause nausea, vomiting, retching or a combination thereof. A serotonin reuptake inhibitor (SRI) is any compound which inhibits the uptake of serotonin. In a particular embodiment, the nausea, vomiting, retching or any combination thereof is asscociated with the onset of SRI therapy. When the SRI is dosed on an as needed basis (prn), each dose can be considered the onset of therapy and can cause nausea, vomiting, retching or any combination thereof. Such pm dosing is typically used in the treatment of premature ejaculation. The SRI can have other therapeutic characteristics such as inhibition of the uptake of noradrenaline. Therefore, SRIs include selective serotonin reuptake inhibitors (SSRIs) such as fluoxetine, paroxetine, sertraline and the rapid onset SSRI dapoxetine. In addition, certain SSRIs are known to exhibit 5-$HT_{1A}$ receptor activities (e.g., antagonist or partial agonist activity at the 5-$HT_{1A}$ receptor). Compounds which have combined SSRI and 5-$HT_{1A}$ receptor activities include those described in WO 99/02516 and WO 02/44170, the contents of which are incorporated herein by reference. These compounds are represented by the Formulas III, IV and V:

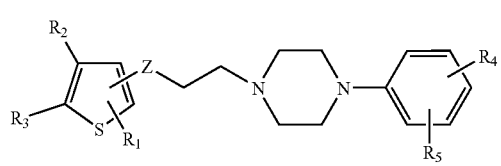

III wherein, Z is —CO—, —CH($OR_6$)— or —C($NOR_7$)—;
$R_1$ is hydrogen, $C_1$–$C_6$ alkyl, halogen or —O—$R_{12}$;
$R_2$ and $R_3$ independently represent hydrogen, $C_1$–$C_6$ alkyl, halogen, nitro or —O—$R_6$ or $R_2$ and $R_3$ are together —$CR_8$=$CR_9$—$CR_{10}$=$CR_{11}$;
R4 and R5 independently represent hydrogen, alkyl, halogen, haloalkyl, —$OR_{12}$, nitro, —$NR_{13}R_{14}$, —$COR_{12}$, —$CO_2R_{12}$; —$SO_2NR_{13}R_{14}$; —$SO_2R_{12}$; —$SR_{12}$, cyano, —$CONR_{13}R_{14}$;
or $R_4$ and $R_5$ together form a benzene ring;
$R_6$ is hydrogen, $C_1$–$C_6$ alkyl, —$CO_2R_{12}$, —C(O)$NR_{13}R_{14}$, naphthyl or phenyl;
$R_7$ is hydrogen or $C_1$–$C_6$ alkyl;
$R_8$, $R_9$, $R_{10}$ and $R_{11}$ are independently hydrogen, $C_1$–$C_6$ alkyl, halogen, —$OR_{12}$, nitro, cyano, —$NR_{13}R_{14}$, —$COR_{12}$, —$CO_2R_{12}SO_2NR_{13}R_{14}$, —$SO_2R_{12}$, —$SR_{12}$, or —$CONR_{13}R_{14}$;
$R_{12}$ is hydrogen, C1–$C_6$ alkyl or phenyl; and
$R_{13}$ and $R_{14}$ are independently hydrogen, $C_1$–$C_6$ alkyl or phenyl or
$R_{13}$ and $R_{14}$ form a ring of 5 or 6 members; or a pharmaceutically acceptable salt or solvate or any isomer (geometric or optical) or polymorph thereof.

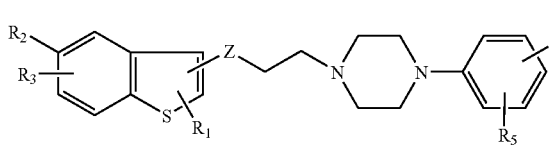

IV wherein, the variables Z, $R_1$, $R_2$, $R_3$, $R_4$ and $R_5$ of Formula IV have the meanings set forth in Formula III.

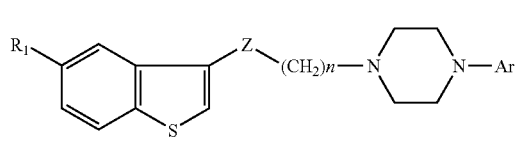

V wherein, n is 1, 2 or 3;
Z is —C(O) or —CHOH;
$R_1$ is hydrogen, $C_1$–$C_6$ alkyl, halogen —$OR_2$, nitro, cyano, —$NR_3R_4$, —$COR_2$, —$CO_2R_2$, —O—$COR_2$, —$SO_2NR_3R_4$, —$SO_2R_2$, —$SR_2$ or —$CONR_3R_4$;
$R_2$ is hydrogen, $C_1$–$C_6$ alkyl or phenyl;
$R_3$ and $R_4$ are independently hydrogen, $C_1$–$C_6$ alkyl or phenyl or
$R_3$ and $R_4$ together form a morpholine, thiomorphone or piperazine ring;
Ar is an optionally substituted bicyclic system formed by a benzocondensed heterocyclic ring with 5, 6 or 7 ring atoms, saturated or unsaturated and containing 1, 2 or 3 heteroatoms selected from N, O or S; or a pharmaceutically acceptable salt or solvate or any isomer (geometric or optical) or polymorph thereof.

Modes of Administration

The compounds for use in the method of the invention can be formulated for oral, transdermal, sublingual, buccal, parenteral, rectal, intranasal, intrabronchial or intrapulmonary administration. For oral administration the compounds can be of the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets can be coated using suitable methods and coating materials such as OPADRY® film coating systems available from Colorcon, West Point, Pa. (e.g., OPADRY® OY Type, OY-C Type, Organic Enteric OY-P Type, Aqueous Enteric OY-A Type, OY-PM Type and OPADRY® White, 32K18400). Liquid preparation for oral administration can be in the form of solutions, syrups or suspensions. The liquid preparations can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

For buccal administration, the compounds for use in the method of the invention can be in the form of tablets or lozenges formulated in a conventional manner.

For parenteral admininstration, the compounds for use in the method of the invention can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

For rectal administration, the compounds for use in the method of the invention can be in the form of suppositories.

For sublingual administration, tablets can be formulated in conventional manner.

For intranasal, intrabronchial or intrapulmonary administration, conventional formulations can be employed.

Further, the compounds for use in the method of the invention can be formulated in a sustained release preparation. For example, the compounds can be formulated with a suitable polymer or hydrophobic material which provides sustained and/or controlled release properties to the active agent compound. As such, the compounds for use the method of the invention can be administered in the form of microparticles for example, by injection or in the form of wafers or discs by implantation.

Additional dosage forms of this invention include dosage forms as described in U.S. Pat. No. 6,340,475, U.S. Pat. No. 6,488,962, U.S. Pat. No. 6,451,808, U.S. Pat. No. 6,340,475, U.S. Pat. No. 5,972,389, U.S. Pat. No. 5,582,837, and U.S. Pat. No. 5,007,790. Additional dosage forms of this invention also include dosage forms as described in U.S. Pat. Application No. 20030147952, U.S. Pat. Application No. 20030104062, U.S. Pat. Application No. 20030104053, U.S. Pat. Application No. 20030044466, U.S. Pat. Application No. 20030039688, and U.S. Pat. Application No. 20020051820. Additional dosage forms of this invention also include dosage forms as described in PCT Patent Application WO 03/35041, PCT Patent Application WO 03/35040, PCT Patent Application WO 03/35029, PCT Patent Application WO 03/35177, PCT Patent Application WO 03/35039, PCT Patent Application WO 02/96404, PCT Patent Application WO 02/32416, PCT Patent Application WO 01/97783, PCT Patent Application WO 01/56544, PCT Patent Application WO 01/32217, PCT Patent Application WO 98/55107, PCT Patent Application WO 98/11879, PCT Patent Application WO 97/47285, PCT Patent Application WO 93/18755, and PCT Patent Application WO 90/11757.

In one embodiment, the dosage forms of the present invention include pharmaceutical tablets for oral administration as described in U.S. Patent Application No. 20030104053. For example, suitable dosage forms of the present invention can combine both immediate-release and prolonged-release modes of drug delivery. The dosage forms of this invention include dosage forms in which the same drug is used in both the immediate-release and the prolonged-release portions as well as those in which one drug is formulated for immediate release and another drug, different from the first, is formulated for prolonged release. This invention encompasses dosage forms in which the immediate-release drug is at most sparingly soluble in water, i.e., either sparingly soluble or insoluble in water, while the prolonged-release drug can be of any level of solubility.

More particularly, in a further embodiment, the prolonged-release portion of the dosage form can be a dosage form that delivers its drug to the digestive system continuously over a period of time of at least an hour and preferably several hours and the drug is formulated as described in in U.S. Patent Application No. 20030104053. In said embodiment, the immediate-release portion of the dosage form can be a coating applied or deposited over the entire surface of a unitary prolonged-release core, or can be a single layer of a tablet constructed in two or more layers, one of the other layers of which is the prolonged-released portion and is formulated as described in U.S. Patent Application No. 20030104053.

In another embodiment of the invention, the supporting matrix in controlled-release tablets or controlled release portions of tablets is a material that swells upon contact with gastric fluid to a size that is large enough to promote retention in the stomach while the subject is in the digestive state, which is also referred to as the postprandial or "fed" mode. This is one of two modes of activity of the stomach that differ by their distinctive patterns of gastroduodenal motor activity. The "fed" mode is induced by food ingestion and begins with a rapid and profound change in the motor pattern of the upper gastrointestinal (GI) tract. The change consists of a reduction in the amplitude of the contractions that the stomach undergoes and a reduction in the pyloric opening to a partially closed state. The result is a sieving process that allows liquids and small particles to pass through the partially open pylorus while indigestible particles that are larger than the pylorus are retropelled and retained in the stomach. This process causes the stomach to retain particles that are greater than about 1 cm in size for about 4 to 6 hours. The controlled-release matrix in these embodiments of the invention is therefore selected as one that swells to a size large enough to be retropelled and thereby retained in the stomach, causing the prolonged release of the drug to occur in the stomach rather than in the intestines. Disclosures of oral dosage forms that swell to sizes that will prolong the residence time in the stomach are found in U.S. Pat. No. 6,448,962, U.S. Pat. No. 6,340,475, U.S. Pat. No. 5,007,790, U.S. Pat. No. 5,582,837, U.S. Pat. No. 5,972,389, PCT Patent Application WO 98/55107, U.S. Patent Application No. 20010018707, U.S. Patent Application No. 20020051820, U.S. Patent Application No. 20030029688, U.S. Patent Application No. 20030044466, U.S. Patent Application No. 20030104062, U.S. Patent Application No. 20030147952, U.S. Patent Application No. 20030104053, and PCT Patent Application WO 96/26718. In particular, gastric retained dosage formulations for specific drugs have also been described, for example, a gastric retained dosage formulation for gabapentin is disclosed in PCT Patent Application WO 03/035040.

Coadministration

In practicing the methods of the invention, coadministration refers to administration of a first amount of a 5-$HT_3$ receptor antagonist compound and a second amount of a NARI compound to treat nausea, vomiting, retching or any combination thereof. Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order. When coadministration involves the separate administration of the NARI and 5-$HT_3$ receptor antagonist, the compounds are administered sufficiently close in time to have the desired therapeutic effect.

Dosing

The therapeutically effective amount or dose of (a) a compound having dual therapeutic modes of action (i.e., 5-$HT_3$ receptor antagonist activity and NARI activity); (b) a 5-$HT_3$ receptor antagonist and NARI in combination; or (c) a NARI alone, will depend on the age, sex and weight of the patient, the current medical condition of the patient and the nature of the nausea, vomiting, retching or any combination thereof being treated. The skilled artisan will be able to determine appropriate dosages depending on these and other factors.

As used herein, continuous dosing refers to the chronic administration of a selected active agent.

As used herein, as-needed dosing, also known as "pro re nata" "pm" dosing, and "on demand" dosing or administration is meant the administration of a therapeutically effective dose of the compound(s) at some time prior to commencement of an activity wherein suppression of nausea, vomiting, retching or any combination thereof would be desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

In a particular embodiment, drug administration or dosing is on an as-needed basis, and does not involve chronic drug administration. With an immediate release dosage form, as-needed administration can involve drug administration immediately prior to commencement of an activity wherein suppression of nausea, vomiting, retching or any combination thereof would be desirable, but will generally be in the range of from about 0 minutes to about 10 hours prior to such an activity, preferably in the range of from about 0 minutes to about 5 hours prior to such an activity, most preferably in the range of from about 0 minutes to about 3 hours prior to such an activity.

For example, a suitable dose of the 5-HT$_3$ receptor antagonist can be in the range of from about 0.001 mg to about 500 mg per day, such as from about 0.01 mg to about 100 mg, for example, from about 0.05 mg to about 50 mg, such as about 0.5 mg to about 25 mg per day. The dose can be administered in a single dosage or in multiple dosages, for example from 1 to 4 or more times per day. When multiple dosages are used, the amount of each dosage can be the same or different.

For example, a suitable dose of the NARI compound can be in the range of from about 0.001 mg to about 1000 mg per day, such as from about 0.05 mg to about 500 mg, for example, from about 0.03 mg to about 300 mg, such as about 0.02 mg to about 200 mg per day. The dose can be administered in a single dosage or in multiple dosages, for example from 1 to 4 or more times per day. When multiple dosages are used, the amount of each dosage can be the same or different.

For example, a suitable dose of the compound having both 5-HT$_3$ receptor antagonist and NARI activity can be in the range of from about 0.001 mg to about 1000 mg per day, such as from about 0.05 mg to about 500 mg, for example, from about 0.03 mg to about 300 mg, such as from about 0.02 mg to about 200 mg per day. In a particular embodiment, a suitable dose of the compound having both 5-HT$_3$ receptor antagonist and NARI activity can be in the range of from about 0.1 mg to about 50 mg per day, such as from about 0.5 mg to about 10 mg per, day such as about 0.5, 1, 2, 3, 4, 5, 6, 7, 8, 9, or 10 mg per day. The dose per day can be administered in a single dosage or in multiple dosages, for example from 1 to 4 or more times per day. When multiple dosages are used, the amount of each dosage can be the same or different. For example a dose of 1 mg per day can be administered as two 0.5 mg doses, with about a 12 hour interval between doses.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

For the compounds having both NARI and 5-HT$_3$ receptor antagonist activity, each dosage can typically contain from about 0.001 mg to about 1000 mg, such as from about 0.05 mg to about 500 mg, for example, from about 0.03 mg to about 300 mg, such as about 0.02 mg to about 200 mg of the active ingredient.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. Dosing can be on demand by the subject.

For the compounds having both NARI and 5-HT$_3$ receptor antagonist activity, each dosage can typically contain from about 0.001 mg to about 1000 mg, such as from about 0.05 mg to about 500 mg, for example, from about 0.03 mg to about 300 mg, such as about 0.02 mg to about 200 mg of the active ingredient.

When the method of treatment comprises coadministration of a NARI and a 5-HT$_3$ receptor antagonist each dose can typically contain from about 0.001 mg to about 1000 mg, such as from about 0.05 mg to about 500 mg, for example, from about 0.03 mg to about 300 mg, such as about 0.02 mg to about to about 200 mg of the NARI and typically can contain from about 0.001 mg to about 500 mg, such as from about 0.01 mg to about 100 mg, for example, from about 0.05 mg to about 50 mg, such as about 0.5 mg to about 25 mg of the 5-HT$_3$ receptor antagonist.

When the method of treatment comprises administration of a NARI alone, each dose can typically contain from about 0.001 mg to about 1000 mg, such as from about 0.05 mg to about 500 mg, for example, from about 0.03 mg to about 300 mg, such as 0.02 to about to about 200 mg of the active ingredient.

The invention further includes a kit for treating nausea, vomiting, retching or any combination thereof. The kit comprises at least one compound having both 5-HT$_3$ receptor antagonist activity and NARI activity (e.g., a single compound) and an instruction insert for administering the compound according to the method of the invention. In addition, the kit can comprise a first compound which is a 5-HT$_3$ receptor antagonist and a second compound which is a NARI and an instruction insert for administering the compounds according to the method of the invention. The first and second compounds can be in separate dosage forms or combined in a single dosage form.

As used herein, the term pharmaceutically acceptable salt refers to a salt of the administered compounds prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

It is understood that 5-HT$_3$ receptor antagonists, NARIs and single compounds having both NARI and 5-HT$_3$ antagonist activities can be identified, for example, by screening libraries or collections of molecules using suitable methods. Another source for the compounds of interest are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

The invention also relates to a method of processing a claim under a health insurance policy submitted by a claimant seeking reimbursement for costs associated with the treatment of nausea, vomiting, retching or any combination thereof, as described herein.

In one embodiment, the method of processing a claim under a health insurance policy submitted by a claimant seeking reimbursement for costs associated with treatment of nausea, vomiting, retching or any combination thereof, wherein said treatment comprises coadministering to a subject a first amount of a 5-$HT_3$ receptor antagonist and a second amount of a noradrenaline reuptake inhibitor, wherein the first and second amounts together comprise a therapeutically effective amount comprising: reviewing said claim; determining whether said treatment is reimbursable under said insurance policy; and processing said claim to provide partial or complete reimbursement of said costs.

In one embodiment, the nausea, vomiting, retching or any combination thereof is caused by an anesthetic, radiation, a cancer chemotherapeutic agent, a toxic agent, an odor, a medicine, pregnancy or motion.

In a particular embodiment, the medicine is selected from the group consisting of an analgesic, an antibiotic, an antifungal or a serotonin reuptake inhibitor.

In another embodiment, the nausea, vomiting, retching or any combination thereof is caused by a condition which is associated with vertigo.

In another embodiment, the nausea, vomiting, retching or any combination thereof is caused by headache.

In yet another embodiment, the nausea, vomiting, retching or any combination thereof is caused by a malady of the gastrointestinal (GI) tract.

The invention also relates to a method for processing a claim under a health insurance policy submitted by a claimant seeking reimbursement for costs associated with treatment of nausea, vomiting, retching or any combination thereof, wherein said treatment comprises coadministering to a subject a therapeutically effective amount of a 5-$HT_3$ receptor antagonist and a therapeutically effective amount of a noradrenaline reuptake inhibitor comprising: reviewing said claim; determining whether said treatment is reimbursable under said insurance policy; and processing said claim to provide partial or complete reimbursement of said costs.

In one embodiment, the nausea, vomiting, retching or any combination thereof is caused by an anesthetic, radiation, a cancer chemotherapeutic agent, a toxic agent, an odor, a medicine, pregnancy or motion.

In a particular embodiment, the medicine is selected from the group consisting of an analgesic, an antibiotic, an antifungal or a serotonin reuptake inhibitor.

In another embodiment, the nausea, vomiting, retching or any combination thereof is caused by a condition which is associated with vertigo.

In another embodiment, the nausea, vomiting, retching or any combination thereof is caused by headache.

In yet another embodiment, the nausea, vomiting, retching or any combination thereof is caused by a malady of the gastrointestinal (GI) tract.

The invention also relates to a method for processing a claim under a health insurance policy submitted by a claimant seeking reimbursement for costs associated with treatment of nausea, vomiting, retching or any combination thereof, wherein said treatment comprises administering to a subject a therapeutically effective amount of a compound having 5-$HT_3$ receptor antagonist activity and noradrenaline reuptake inhibitor activity comprising: reviewing said claim; determining whether said treatment is reimbursable under said insurance policy; and processing said claim to provide partial or complete reimbursement of said costs.

In a particular embodiment, the compound having 5-$HT_3$ receptor antagonist activity and noradrenaline reuptake inhibitor activity is MCI-225.

In one embodiment, the nausea, vomiting, retching or any combination thereof is caused by an anesthetic, radiation, a cancer chemotherapeutic agent, a toxic agent, an odor, a medicine, pregnancy or motion.

In a particular embodiment, the medicine is selected from the group consisting of an analgesic, an antibiotic, an antifungal or a serotonin reuptake inhibitor.

In another embodiment, the nausea, vomiting, retching or any combination thereof is caused by a condition which is associated with vertigo.

In another embodiment, the nausea, vomiting, retching or any combination thereof is caused by headache.

In yet another embodiment, the nausea, vomiting, retching or any combination thereof is caused by a malady of the gastrointestinal (GI) tract.

The invention further relates to a method for processing a claim under a health insurance policy submitted by a claimant seeking reimbursement for costs associated with treatment of nausea, vomiting, retching or any combination thereof, wherein said treatment comprises administering to a subject a therapeutically effective amount of a noradrenaline reuptake inhibitor, wherein the noradrenaline reuptake inhibitor characterized by the substantial absence of anticholinergic effects comprising: reviewing said claim; determining whether said treatment is reimbursable under said insurance policy; and processing said claim to provide partial or complete reimbursement of said costs.

In one embodiment, the nausea, vomiting, retching or any combination thereof is caused by an anesthetic, radiation, a cancer chemotherapeutic agent, a toxic agent, an odor, a medicine, pregnancy or motion.

In a particular embodiment, the medicine is selected from the group consisting of an analgesic, an antibiotic, an antifungal or a serotonin reuptake inhibitor.

In another embodiment, the nausea, vomiting, retching or any combination thereof is caused by a condition which is associated with vertigo.

In another embodiment, the nausea, vomiting, retching or any combination thereof is caused by headache.

In yet another embodiment, the nausea, vomiting, retching or any combination thereof is caused by a malady of the gastrointestinal (GI) tract.

Pharmacological Methods

Anti-Emetic Effects

The activity of compounds as anti-emetics can be demonstrated by any suitable model. For example, the extent to which compounds can reduce the latency or the number of retches and/or vomits induced by emetogens (e.g., cisplatin which is a typically used emetogenic trigger in suitable animal models) in, for example, the dog (e.g., beagles), the piglet or in the ferret can be assessed. For example, suitable methods are described in Tatersall et al. and Bountra et al., *European Journal of Pharmacology*, 250: (1993) R5 and 249:(1993) R3–R4 and Milano et al., *J. Pharmacol. Exp. Ther.*, 274(2): 951–961 (1995).

In addition, the general method described by Florezyk et al., *Cancer Treatment Report*, 66(1): 187–9, (1982)) and summarized below, can also be used to assess effect of a test compound on emesis in the ferret.

Briefly, both the test compound and cisplatin are prepared and administered. The cisplatin is a representative emetogenic trigger for vomiting.

a) Control—Without Test Agent

Emesis is induced in groups of 6 male ferrets weighing about 2 kg, by intravenous administration of cisplatin at a suitable dose (e.g., 10 mg/kg). The onset of emesis is noted. Over a period of 2 hours the number of vomits/retches (episodes) is recorded. Behavioral changes characteristic of emesis are also noted.

b) With Test Compound

The test compound is administered to groups of 6 male ferrets weighing about 2 kg, by intravenous administration at suitable doses immediately prior to administration of cisplatin as described above. The animals are observed for 3 hours.

The emetic response seen in drug tested and control animals can then be compared to assess antiemetic properties of the test compound.

Exemplification

The present invention will now be illustrated by the following Example, which is not intended to be limiting in any way.

Treatment of Vomiting and Retching Using MCI-225

The ability of MCI-225 to reduce retching and vomiting in an accepted model of cytotoxin-induced emesis in the ferret was assessed. Specifically, the experiments described herein investigated the effect of MCI-225 on retching and vomiting induced by cisplatin. Ondansetron was used as a positive control in the model, in view of its known antiemetic activity.

Animals

Adult male ferrets (*Mustela putariofuro*) weighing 1200–1880 g were purchased from Triple F Farms (Sayre, Pa.) and housed in individual cages at standardized conditions (12:12 h light/dark cycle and 21–23° C.). Prior to the experiments, the ferrets were allowed a 7–10 day acclimatization period to the animal facility. The ferrets were fed a carnivore diet with free access to food and water throughout the course of the study. The use of the ferret model of emesis and the drug treatment were preapproved in accordance with facility standards.

Cisplatin-Induced Emesis

A cisplatin solution was prepared by adding preheated (70° C.) saline to cisplatin powder (Sigma-Aldrich Co.) and stirring or sonicating at 40° C. until dissolved.

Following administration of the cisplatin and either MCI-225, ondansetron or vehicle alone, the occurrence of retching and vomiting was monitored for a period of 6 hours. Retching was defined as the number of forceful rhythmic contractions of the abdomen occurring with the animal in characteristic posture, but not resulting in the expulsion of upper gastrointestinal tract contents (Watson et al., *British Journal of Pharmacology*, 115(1): 84–94 (1994)). Vomiting was defined as the forceful oral expulsion of upper gastrointestinal contents. The latency of the retching or vomiting response and the number of episodes were recorded for each animal and summarized for each experimental group (Wright et al., *Infect. Immun.*, 68(4): 2386–9 (2000)).

Drug Treatment

Following one hour of acclimation to the observation cage, ferrets received an intraperitoneal (i.p.) injection of cisplatin (5 mg/kg in 5 mL) followed in about 2 minutes by i.p. injection of a single dose of MCI-225 or ondansetron (Rudd and Naylor, *Eur. J. Pharmacol.*, 322: 79–82 (1997)). Dose-response effects of MCI-225 dosed at 1, 10 and 30 mg/kg i.p. in a 0.5 ml/kg solution or ondansetron dosed at 5 and 10 mg/kg i.p. in a 0.5 mL/kg solution were studied. Each animal received a single-dose drug treatment. In addition, three animals received an initial dose (30 mg/kg i.p.) and a second MCI-225 injection (30 mg/kg i.p.) 180 minutes following the initial dose. Control animals were treated with cisplatin followed by vehicle alone (propanediol dosed in a 0.5 mL/kg solution). All groups were randomized.

Results

Vehicle Alone

Figure 2:
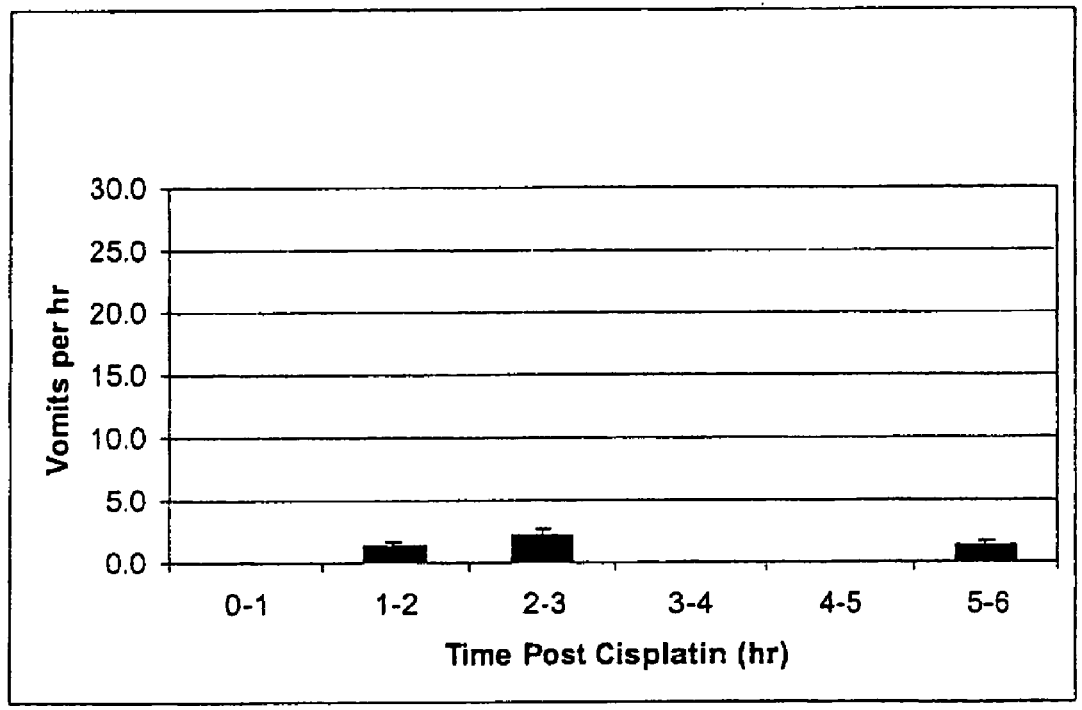
FIG. 2 is a bar graph of cisplatin-induced vomits per hour versus time (hours) post administration of cisplatin in male ferrets treated with a 5 mg/kg dose of cisplatin and vehicle.

Cisplatin induced an emetic response in 100% of the animals receiving vehicle. The mean response was characterized by a total number of 42.8±8.1 events (both retches and vomits), which occurred during the observation period. The mean latency of the first response was 133±22 min post-cisplatin administration. The time-course of acute emetic events appearing in response to cisplatin is summarized in FIG. 1 (retches) and FIG. 2 (vomits).

Ondansetron

Figure 3:
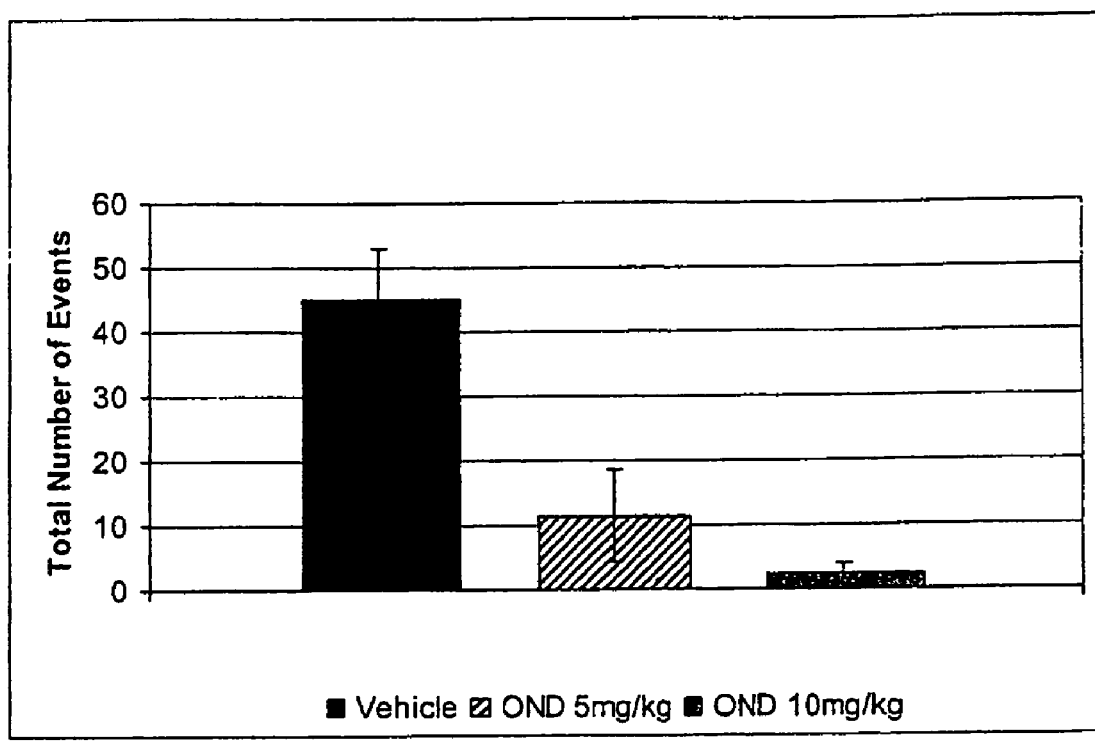
FIG. 3 is a bar graph of the total number of cisplatin-induced emetic events (retches and vomits combined) in male ferrets treated with cisplatin at a dose of 5 mg/kg followed by ondansetron at 5 mg/kg or 10 mg/kg or vehicle alone.
Figure 4:
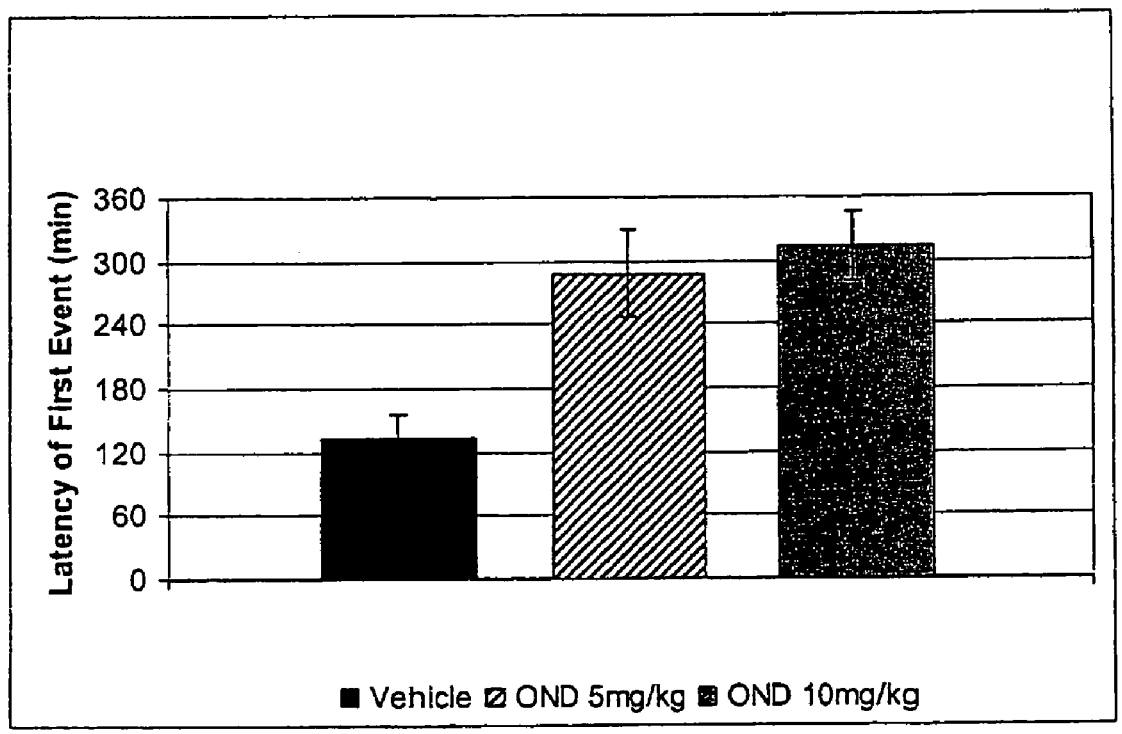
FIG. 4 is a bar graph of the effect of ondanseton on the latency of the first cisplatin-induced emetic event (retch or vomit) in male ferrets treated with cisplatin at a dose of 5 mg/kg followed by ondansetron at 5 mg/kg or 10 mg/kg or vehicle alone.

Ondansetron applied at the 5 mg/kg and 10 mg/kg dose-dependently reduced the number of emetic events induced by cisplatin. The effect of ondansetron was accompanied by an increase in the latency of the first emetic response following cisplatin treatment. The results are set forth in Table 1 (*p<0.05). and presented graphically in FIG. 3 and FIG. 4.

TABLE 1

| No. of Animals (N) | Treatment | Retches (360 min) | Vomits (360 min) | Total Events | Latency (min) |
|---|---|---|---|---|---|
| N = 10 | Vehicle | 42.8 ± 8.1 | 3.3 ± 0.8 | 46.1 ± 7.8 | 133 ± 22 |
| N = 7 | Ondansetron (5 mg/kg) | 11.2 ± 7.0 | 0.3 ± 0.2 | 11.5 ± 7.2 | 288 ± 4 |
| N = 7 | Ondansetron (10 mg/kg) | 2.4 ± 1.6 | 0.0 ± 0.0 | 2.4 ± 1.6* | 313 ± 32 |

MCI-225

Figure 5:
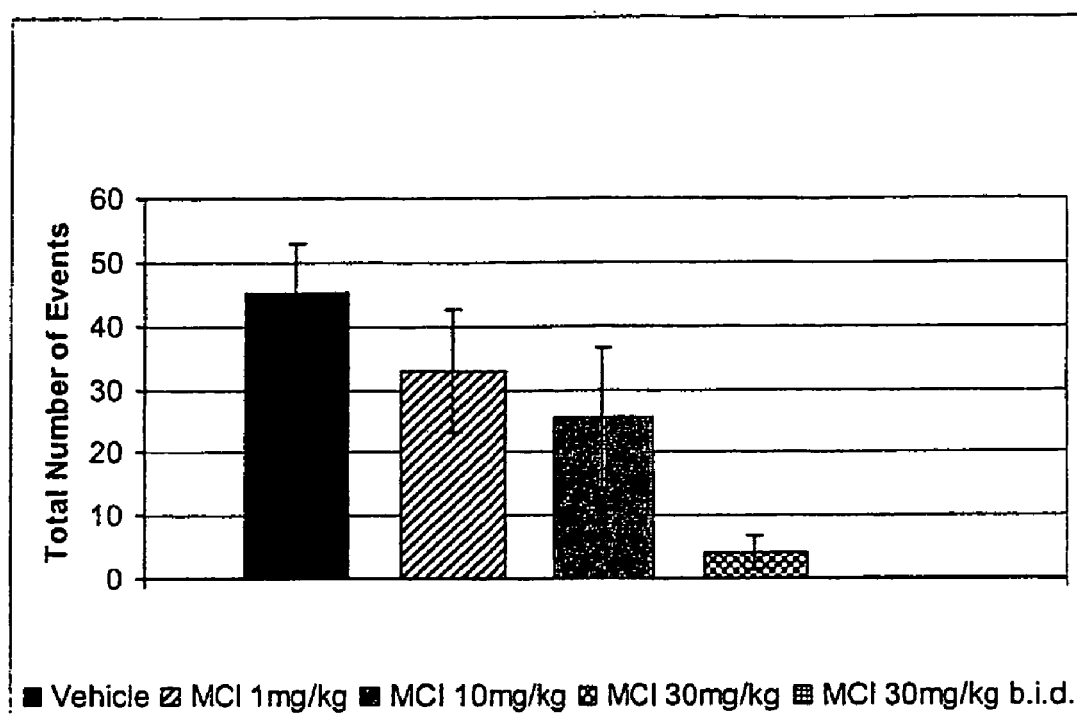
FIG. 5 is a bar graph of the total number of cisplatin-induced emetic events (retches and vomits combined) in male ferrets treated with cisplatin at a dose of 5 mg/kg followed by a single dose of MCI-225 (1 mg/kg, 10 mg/kg or 30 mg/kg), two 30 mg/kg doses at 3 hour intervals or vehicle alone.
Figure 6:
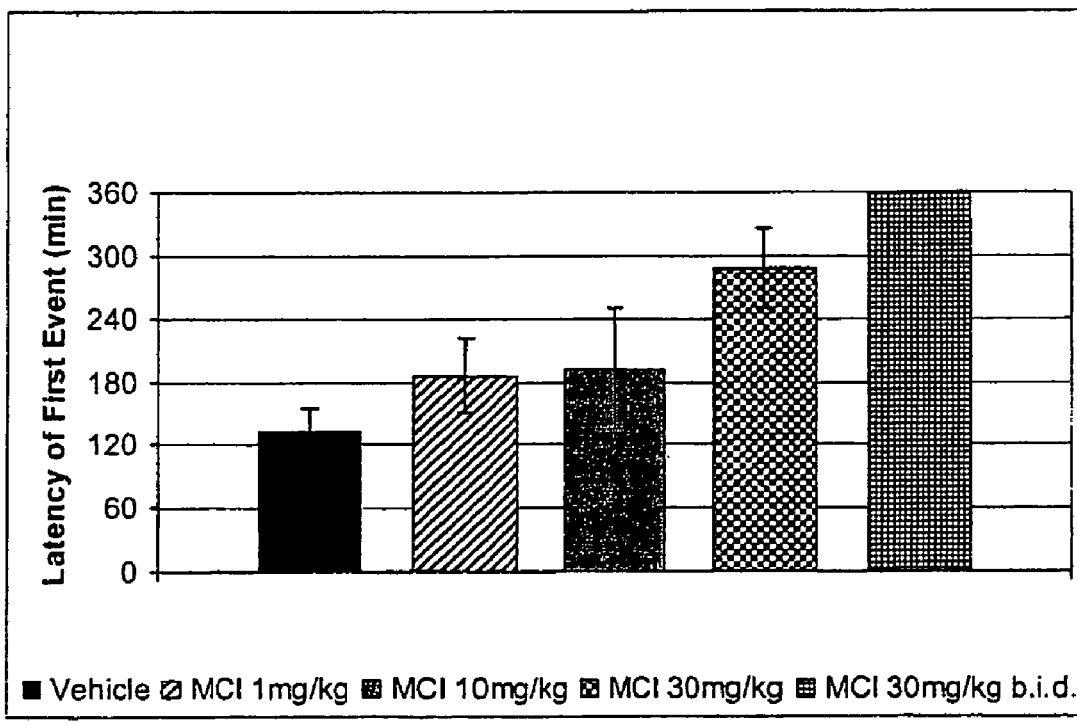
FIG. 6 is a bar graph of the effect of ondansetron on the latency of the first cisplatin-induced emetic event (retch or vomit) in male ferrets treated with cisplatin at a dose of 5 mg/kg followed by a single dose of MCI-225 (1 mg/kg, 10 mg/kg or 30 mg/kg), two 30 mg/kg doses at 3 hour intervals or vehicle alone.

As set forth in Table 2, administration of MCI-225 at concentrations of 1, 10 or 30 mg/kg caused dose-dependent reduction in the retches and vomits induced by cisplatin (*p<0.05). The emetic response was eliminated by administration of two doses of 30 mg/kg, applied b.i.d at a 180-min interval. The decrease in the number of emetic events induced by MCI-225 was accompanied by an increase in the latency of the response. The results are set forth in Table 1 in FIG. 5 and FIG. 6.

TABLE 2

| No. of Animals (N) | Treatment | Retches (360 min) | Vomits (360 min) | Total Events | Latency (min) |
|---|---|---|---|---|---|
| N = 10 | Vehicle | 42.8 ± 8.1 | 3.3 ± 0.8 | 46.1 ± 7.8 | 133 ± 22 |
| N = 10 | MCI-225 (1 mg/kg) | 30.4 ± 9.1 | 2.5 ± 0.7 | 32.9 ± 9.8 | 186 ± 35 |
| N = 10 | MCI-225 (10 mg/kg) | 22.9 ± 10.3 | 2.6 ± 1.0 | 25.5 ± 11.1 | 192 ± 57 |
| N = 11 | MCI-225 (30 mg/kg) | 3.3 ± 2.2 | 0.7 ± 0.5 | 4.0 ± 2.6* | 287 ± 38 |
| N = 3 | MCI-225 (30 mg/kg b.i.d) | 0.0 ± 0.0 | 0.0 ± 0.0 | 0.0 ± 0.0 | 360 ± 0 |

CONCLUSION

The results set forth in Tables 1 and 2 show that MCI-225 is effective at reducing retching and vomiting in an accepted animal model of emesis, using a similar dose range as the positive control (ondansetron). Thus, MCI-225 can be used in the treatment of nausea, vomiting, retching or any combination thereof in a subject.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the treatment of nausea and vomiting in a patient suffering therefrom, comprising administering to the patient an effective amount of 4-(2-fluorophenyl)-6-methyl-2-(1-piperazinyl)thieno[2,3-D]pyrimidine or a salt thereof.

2. A method for the treatment of chemotherapy- or radioactivity-induced emesis in a patient suffering therefrom, comprising administering to the patient an effective amount of 4-(2-fluorophenyl)-6-methyl-2-(1-piperazinyl)thieno[2,3-D]pyrimidine or a salt thereof.

3. The method according to claims 1 or 2, wherein the salt is the hydrochloride monohydrate.

* * * * *